(12) United States Patent
Hilliard

(10) Patent No.: US 7,077,646 B2
(45) Date of Patent: Jul. 18, 2006

(54) AUTOMATED METHOD FOR PRODUCING IMPROVED ORTHODONTIC ALIGNERS

(76) Inventor: Jack Keith Hilliard, 330 E. Highlands Dr., Lakeland, FL (US) 33813

( * ) Notice: Subject to any disclaimer, the term of this patent is extended or adjusted under 35 U.S.C. 154(b) by 10 days.

(21) Appl. No.: 10/926,462

(22) Filed: Aug. 25, 2004

(65) Prior Publication Data

US 2005/0048433 A1 Mar. 3, 2005

Related U.S. Application Data

(60) Provisional application No. 60/498,781, filed on Aug. 29, 2003.

(51) Int. Cl.
*A61C 3/00* (2006.01)
(52) U.S. Cl. .................................. 433/6; 433/18
(58) Field of Classification Search .............. 433/6, 433/18, 24
See application file for complete search history.

(56) References Cited

U.S. PATENT DOCUMENTS

| | | |
|---|---|---|
| 1,463,968 A | 8/1923 | Petry |
| 2,257,709 A | 9/1941 | Anderson |
| 2,467,432 A | 4/1949 | Kesling |
| 2,479,780 A | 8/1949 | Remensnyder |
| 3,178,820 A | 4/1965 | Kesling |
| 3,407,500 A | 10/1968 | Kesling |
| 3,510,946 A | 5/1970 | Kesling |
| 3,574,941 A | 4/1971 | Ritter |
| 3,724,075 A | 4/1973 | Kesling |
| 3,950,851 A | 4/1976 | Bergersen |
| 3,991,471 A | 11/1976 | Hoops |
| 4,055,895 A | 11/1977 | Huge |
| 4,505,672 A | 3/1985 | Kurz |
| 4,591,341 A | 5/1986 | Andrews |
| 4,755,139 A | 7/1988 | Abbatte et al. |
| 4,793,803 A | 12/1988 | Martz |
| 5,139,419 A | 8/1992 | Andreiko et al. |
| 5,242,304 A | 9/1993 | Truax et al. |
| 5,536,168 A | 7/1996 | Bourke |
| 5,683,243 A * | 11/1997 | Andreiko et al. ............... 433/3 |
| 5,683,244 A | 11/1997 | Truax |
| 5,692,894 A | 12/1997 | Schwartz et al. |
| 5,863,198 A | 1/1999 | Doyle et al. |
| 5,879,158 A | 3/1999 | Doyle et al. |
| 5,975,893 A | 11/1999 | Chishti et al. |
| 6,183,248 B1 * | 2/2001 | Chishti et al. ................. 433/6 |
| 6,217,325 B1 | 4/2001 | Chishti et al. |
| 6,293,790 B1 | 9/2001 | Hilliard |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,318,995 B1 | 11/2001 | Sachdeva et al. |
| 6,390,812 B1 * | 5/2002 | Chishti et al. ................. 433/6 |
| 6,398,548 B1 | 6/2002 | Muhammad et al. |
| 6,582,227 B1 * | 6/2003 | Phan et al. .................... 433/24 |

(Continued)

FOREIGN PATENT DOCUMENTS

WO WO 99/42055 8/1999

*Primary Examiner*—Ralph A. Lewis
(74) *Attorney, Agent, or Firm*—Dorr, Carson & Birney, P.C.

(57) ABSTRACT

A method for producing orthodontic aligners uses a CAD system to modify a digital model of the patient's oral anatomy to incorporate features that accommodate attachment of aligner auxiliaries to the completed aligner(s).

23 Claims, 13 Drawing Sheets

U.S. PATENT DOCUMENTS

| | | |
|---|---|---|
| 6,702,575 B1 | 3/2004 | Hilliard |
| 6,705,863 B1 * | 3/2004 | Phan et al. .................. 433/24 |
| 6,830,450 B1 * | 12/2004 | Knopp et al. .................. 433/6 |
| 6,947,038 B1 * | 9/2005 | Anh et al. .................. 345/419 |

* cited by examiner

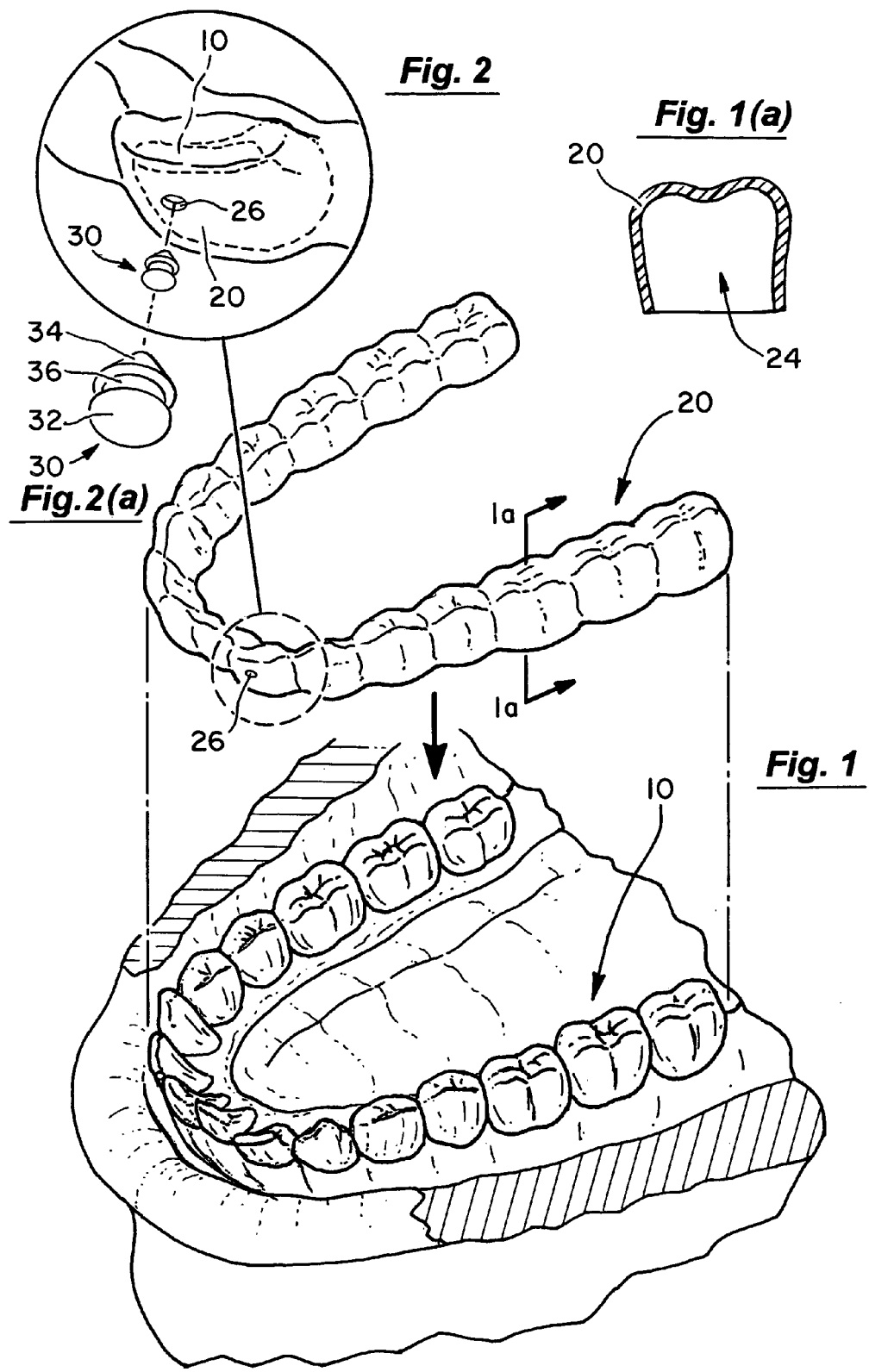

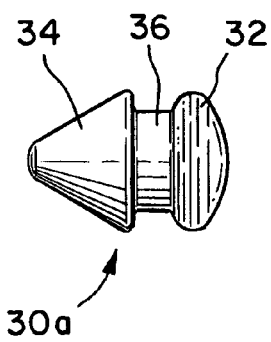 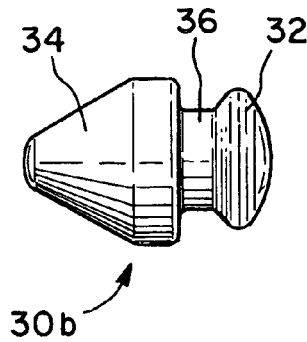 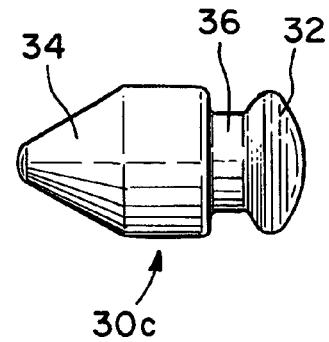
*Fig. 3(a)*     *Fig. 3(b)*     *Fig. 3(c)*
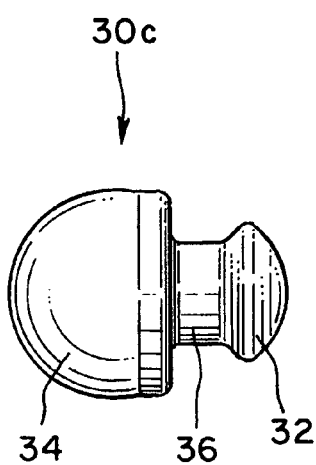 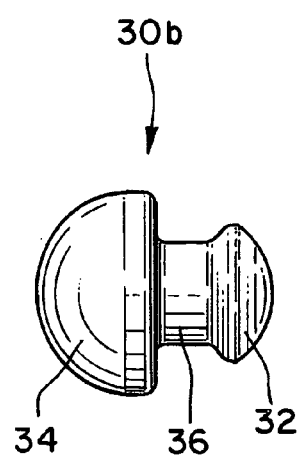 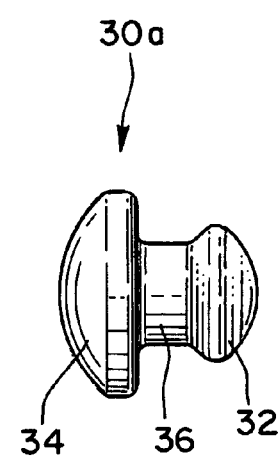
*Fig. 4(c)*     *Fig. 4(b)*     *Fig. 4(a)*

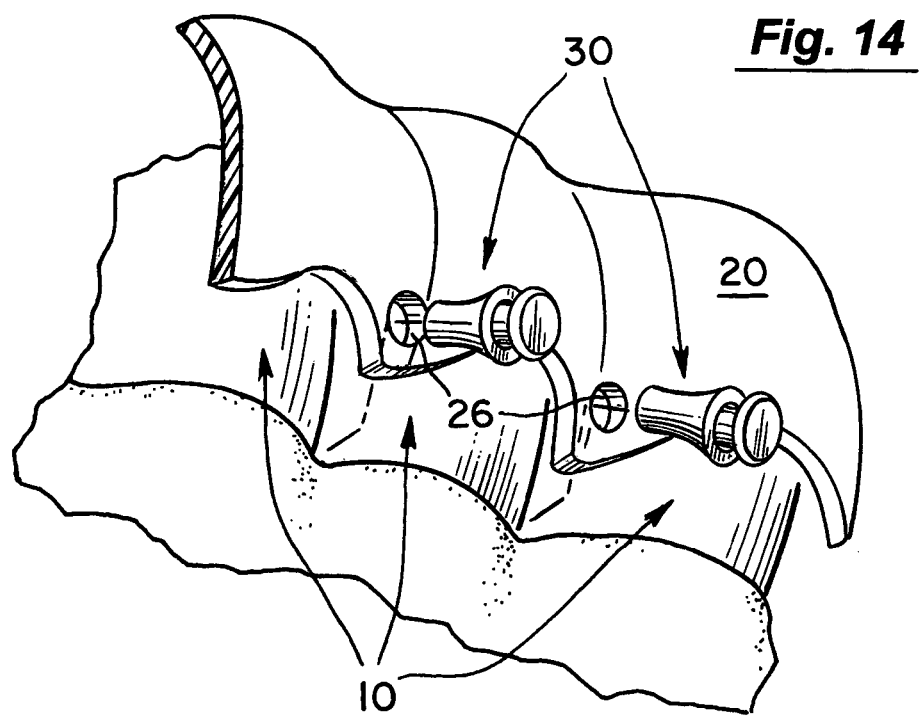
Fig. 14
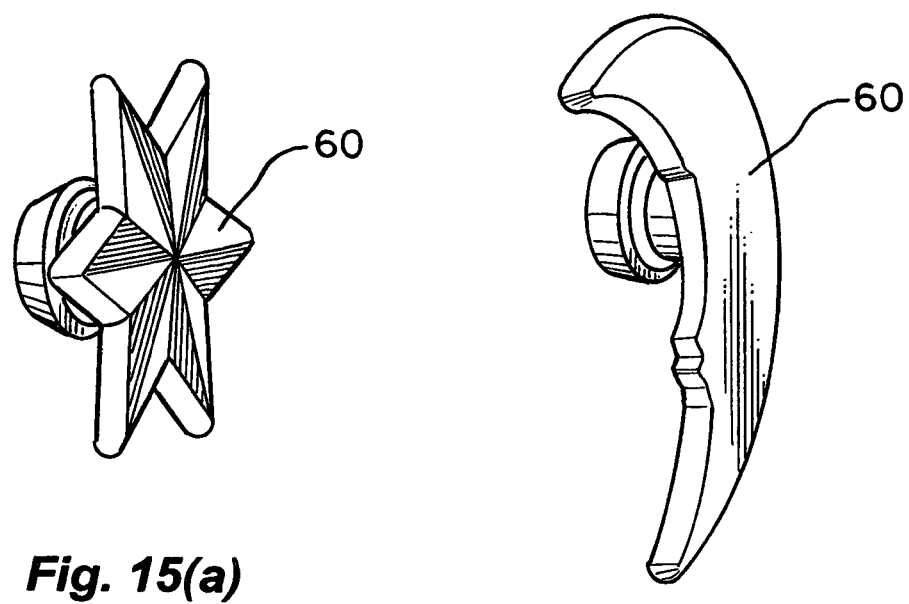
Fig. 15(a)
Fig. 15(b)

AUTOMATED METHOD FOR PRODUCING IMPROVED ORTHODONTIC ALIGNERS

RELATED APPLICATION

The present application is based on, and claims priority to the Applicant's U.S. Provisional Patent Application 60/498,781, entitled "Automated Methods for Producing Improved Orthodontic Aligners," filed on Aug. 29, 2003.

BACKGROUND OF THE INVENTION

1. Field of the Invention

The present invention relates generally to the field of orthodontics. More specifically, the present invention discloses a method for producing improved orthodontic aligners.

2. Background of the Invention

Like many areas involving the delivery of healthcare, the field of dentistry is currently involved in a process of rapid change in what has until recently been considered conventional practice. Such changes are taking place in many fields and are often the result of, and are driven by the integration of new computer-based digital technologies, which tend to become the core of powerful new methodologies. In the dental specialty of orthodontics, for example, the process of laser scanning and the three-dimensional imaging of a patient's teeth and then the manipulation of the virtual tooth positions within a computer-aided-design (CAD) environment is an example. Commercial orthodontic service centers have emerged that provide new types of services for orthodontists based on such computer driven three-dimensional imaging methods. These new commercial enterprises, based on three-dimensional imaging and CAD manipulation of tooth positions and tooth relationships have become routinely used by orthodontists and some dentists as part of a successful new "computer perfect" approach to straightening teeth. The integration of these digital services into orthodontics has been commercially successful, and many clinicians feel that utilization of these new 3D imaging-based technologies has led to a higher standard of care.

To use the newly-available digital services, an orthodontist's support staff first takes an impression of a patient's teeth, gums and soft tissue. From the impression, a positive stone model is poured and allowed to cure. Instead of retaining a patient's models for in-office case diagnosis and treatment planning as in the past, the attending orthodontist will instead ship the patient's models to a regional commercial orthodontic service center. A number of services are available to a doctor using such service centers, and these services will be provided according to a prescription and other instructions sent along with the patient's models to the service center.

As is the case in most areas of healthcare, it is not uncommon for the introduction of a central technological improvement to drive a reassessment and revision of what had previously been considered standard and accepted practice. When technology-driven changes occur within a specialized field, some of the conventional procedures routinely used in the past may be rendered unnecessary by the technological innovation and are dropped. Other established procedures however may happen to integrate well with the new technology and are thereby themselves augmented, improved and retained alongside the new practices. The present invention, to be described in full detail below consists of new methods based on a combination of past practices and computer-based three-dimensional imaging and related CAD-based procedures. Stated differently, the present invention can be viewed as being a synthesis of the new digital methods with conventional methods that in combination create an improved methodology for delivering orthodontic therapy.

Andreiko et al. To fully appreciate the advantages of the present invention, consider U.S. Pat. No. 5,139,419 (Andreiko et al). Andreiko et al. disclose a methodology beginning with scanning of a patient's models as described above to produce a digital code that can be assimilated by the computer software. For this step, models can be scanned by any of several current methods to create digital code representing a virtual model of the teeth, gums and soft tissues that can be visually displayed on a computer screen. Andreiko et al. describe methods for the virtual separation of individual teeth from adjacent teeth and soft tissues, and methods for bodily repositioning of individual teeth and groups of teeth.

Generally, Andreiko et al. describe gross movements of groups of teeth establishing or correcting factors such as arch width and arch shape. Next, individual teeth are torqued, tipped, rotated, intruded or extruded and otherwise bodily repositioned according to known standards and established criteria. Next, gnathological fine-tuning of positions of the teeth of one arch relative to the teeth of the other arch is accomplished so the upper and lower teeth will interdigitate in a stable and centric relationship. The purpose of these procedures is to arrive at an ideal post-treatment condition in the form of a finished, virtual model within the CAD software. Andreiko et al. describe methodologies for the use of such digitally-produced results that constitute the operational foundation of the new commercial orthodontic service centers described above, as well as other uses such as the fabrication of customized orthodontic hardware such as archwires and brackets custom-tailored and fabricated for treatment of an individual patient.

Doyle et al. Other developments using digitally-derived treatment objectives can be understood by examining U.S. Pat. Nos. 5,863,198 and 5,879,158 to Doyle et. al. Orthodontists and their staff understand that the accuracy with which orthodontic brackets are positioned on the teeth largely determines the quality of the case when finished, and it is well known that human error is always involved in the process of direct (manual) bonding.

Doyle et al. describe methods for using the output of the digital methodologies to improve the accuracy with which brackets can be placed. From a process that begins similarly to the process described by Andreiko et al., digital output representing the idealized occlusion is used to provide targets for the placement of virtual brackets on the virtual teeth. Once positioned, the resulting three-dimensional CAD surfaces are used to define placement jigs. The digital code representing the virtually-treated ideal occlusion and the virtually-placed brackets is used to drive an industrial machine tool. The industrial machine tool, such as a CNC-driven milling machine is employed by Doyle et al. to form patient-specific and tooth-specific orthodontic bracket placement jigs. These positioning jigs, or "bonding" jigs are used by orthodontists during the bonding step where orthodontic brackets are bonded to each individual tooth. These methods represent another means of transferring a virtually determined "computer-perfect" treatment configuration to the actual oral realities of an individual. These methods and devices take bracket positioning to new levels of bracket placement precision that is beyond what any individual person is capable of using manual methods.

Orometrix®. One of the commercial efforts to bring scanning and three-dimensional imaging technology into orthodontics is known as the Orometrix® program. Orometrix first was structured as a joint venture with a German company that had developed a successful numerically-controlled custom archwire bending machine. That technology was combined into a system including a new type of hand-held oral scanner and a new type of scanning methodology. The commercializing company has been known by several names including Orometrix, Syrinx and Sure Smile. This combination of technologies is covered by a series of patents beginning with U.S. Pat. Nos. 6,315,553 and 6,318,995 to Sachdeva. This system is based on a inter-oral handheld scanning wand connected to a computer with accompanying software. To use the system, an orthodontist holds the working end of the wand in close proximity to the patient's posterior teeth and then the wand is slowly moved forward, around the front of the arch, and then around to the posterior teeth of the other side of the arch. Software associated with the inter-oral scanning wand stitches one frame to the next and in the process, a three-dimensional image of the entire dental arch and gums is created. As can be appreciated, a scanning method as taught by Sachdeva could be used to scan a patient's models in the setting of a commercial orthodontic service center, or more practically, the inter-oral wand could be used at chair side to scan a patient's teeth directly. In such as case, the resulting three-dimensional image obtained from this scanning method could be forwarded to a commercial service center for processing according to the present invention via the internet.

Invisalign®. Yet another example of the orthodontic application of digital technologies is seen in the commercial service known as the Invisalign® program. The Invisalign® program is based on U.S. Pat. No. 5,975,893 (Chishti et al.), and the many related patents, including in particular U.S. Pat. No. 6,398,548 (Muhammad et al.). As with the other approaches described above, the Invisalign program involves the presentation of a patient's virtually-treated finished occlusion. From that, output methodologies are used to fabricate a series progressive polymeric tooth aligners. Such aligners, sometimes called positioners, are generally similar in appearance to appliances known as mouth guards worn by athletes or the soft plastic appliances worn to protect the teeth against the destructive effects of bruxism. The terms "aligner" and "positioner" are can be viewed as being largely synonymous. An example of an Invisalign aligner 20 is shown generally in FIG. 1. The removable aligner 20 has a polymeric shell with a plurality of cavities 24 to receive the patient's teeth 10, as illustrated in FIG. 1(a). The aligner 20 can be used to engage the patient's upper teeth, lower teeth, or a subset of either of these. However, unlike FIGS. 1, 2, and 2(a), conventional Invisalign aligners do not include openings 26 or aligner auxiliaries 30, as will be described in greater detail below.

The Invisalign® program is marketed as a viable alternative to conventional braces-type orthodontics and is referred to during TV commercials as "invisible braces." The Invisalign tooth aligners are thin, transparent U-shaped plastic appliances formed over patterns or models of the virtual teeth using a combination of vacuum, pressure and heat informally referred to as the "suck down" process and as such, they are considered suck-down appliances. The term "suck down" also is related to the type of dental laboratory machine on which aligners are formed, such as a Biostar-type machine. The Invisalign-type tooth aligners are formed from a thinner material than mouth guard-type appliances. It is a harder but still relatively flexible and somewhat elastic polymeric material similar to polycarbonate (PC). Other materials are sometimes used for certain phases of the Invisalign process.

In order to produce a series of aligners, an Invisalign technician first scans a patient's model as a means to obtain a CAD-manipulatable virtual model of the patient's teeth, gums and soft tissue not unlike Andreiko et al. and Doyle et al. Like the methods taught by Andreiko et al., such a digital model can be displayed and altered using the software tools of a computer aided design (CAD) system. Once the virtual model of the original malocclusion has been established, an Invisalign technician will then undertake steps involving manipulation of the virtual malocclusion ultimately arriving at a finished or ideal occlusion for that patient, similar to the steps taken by Andreiko et al. and Doyle et al. The finished occlusion, even though virtual, is nonetheless consistent with the full repositioning of the occlusion that would result at the end of a successful active treatment phase.

As can be appreciated, after the steps described above are accomplished, an Invisalign technician has two versions of the patient's teeth available within the virtual CAD environment: One of these represents the original malocclusion and the other represents the ideal occlusion that could be expected at the end of successful orthodontic treatment (i.e., the "beginning" and the desired "end" conditions).

It must be noted that the Invisalign technician is not a trained orthodontist. Since the three-dimensional imaging and the corrected case are virtual, they can easily be made available online to the doctor. Using a special viewing and metrix software package provided to the doctor through the internet, the doctor can examine the correctness and precision of the work performed by the Invisalign technician in great detail. The doctor can approve the work performed by the technician, or provide additional instructions to insure that the assumptions of the technician are consistent with the doctor's original treatment plan. In fact, the doctor at one point in the process must provide his formal approval for the process to continue.

After the attending doctor approves the virtual finished occlusion via the internet or other conventional means, the next step in the Invisalign process involves the creation of typically 15 to 25 incremental progressive physical models. Each of these models represents a snap shot of the patient's occlusion at certain stages along his or her treatment sequence between the "beginning" and "end" conditions as described above. To accomplish this, the Invisalign technician will create a virtual "first transition model" that sees a slight repositioning of all or most of the teeth. This first transition model sees some or all of the teeth being subtly moved from their original pre-treatment positions to a virtual first transition position that is in the direction of their intended finished positions. Similarly, a second virtual transition model is created that represents the teeth moved again slightly further in desired directions. The objective of the Invisalign technician is to create the series of progressive models, each biased slightly further than the previous one, each moving the teeth toward their final finished ideal position. A final model will take the teeth from the series of intermediate positions and move them into their final, desired positions.

Once such a series of intermediate models, and a final model are created by the technician, the digital code representing each of the models in the series is directed to operate a type of computer numerically-controlled (CNC) machines, known as rapid prototyping machines. Within the rapid prototyping machines, physical models are grown using one of a group of known processes generally called stereo lithography or 3D printing. The growing step results in the production of a hard, physical duplicate of each of the series of virtual intermediate models and the final model. These are not virtual models. Rather, they are hard, physical models that can be held by hand.

The next step of the Invisalign process sees each of the series of physical models being in turn mounted in suck-down machines where a combination of pressure, heat and vacuum is used to form actual progressive aligners. Each of the series of physical models is used to form a corresponding series of actual aligners. Once the series of progressive aligners are formed and trimmed, they are sequentially labeled, packaged and shipped to the attending orthodontist. The orthodontist then schedules an appointment for the patient, at which time aligner-retaining devices are installed and the aligners and instructions for their use are given to the patient.

The patient will be instructed to begin wearing the first of the series of aligners for a period of time lasting typically two weeks. After that, the first aligner is discarded and the patient transitions to the next aligner of the series and so on.

The aligners serve to urge the patient's teeth to move accordingly. The teeth are progressively biased and urged to move in desired directions toward their predetermined finished positions by the resilience of the polymeric material of the aligners. In response to the gentle but continuous forces delivered by the aligners, certain physiological processes involving the creation and resorbtion of underlying supportive bone are initiated. The net result is the slow orthodontic movement of the roots of the teeth through the underlying bone.

The orthodontist's role in progressive aligner-based treatment is essentially reduced to that of monitoring the physiological response of the teeth and monitoring the patient's level of cooperation with the treatment schedule. In this monitoring mode, however, the attending orthodontist is not required to establish the progressive sequence or otherwise direct the treatment, because the functionality of the aligners and tooth-moving protocol is determined off-site by the Invisalign technician at the orthodontic service center.

Kesling. The Invisalign process involves a treatment modality based on tooth aligners, whose origins can be traced back in time to the positioner-based therapy introduced in the late 1940's by Dr. Peter Kesling. Kesling's positioners used the materials of the day, such as vulcanized rubber. They were generally bulky, one-piece unsightly appliances, as shown for example in U.S. Pat. No. 3,724, 075. Later in the 1970's and 1980's, generally based on the research of Japanese orthodontists, thinner aligners came into use where one aligner was directed to the upper arch and a separate one seated on the lower arch. These aligners were cast in pressure pots and were formed by catalyzing medical grade silicone rubber and other similar biocompatible elastomeric materials. More recently, aligners have been formed from thin, relatively hard, but still elastically flexible materials using the suck-down process. These new materials and the suck-down process for forming are used in the Invisalign program for example.

Since the introduction of positioners by Kesling, all aligners that have been used to positively move teeth (as opposed to retaining or holding teeth once ideally positioned) exhibit tooth-accepting female sockets formed in the aligner. Such sockets are sized to accommodate a single, corresponding tooth, but are intentionally slightly out of register with the actual tooth position. To explain the purpose of this out-of-register relationship and how it is achieved, it is important to understand the conventional or "manual" process for producing progressive aligners which is described below.

Before the current integration of computer-based digital fabrication methods were introduced, aligners were fabricated by the orthodontic support laboratories or by in-practice laboratories. The steps used by a laboratory technician in forming a tooth aligner begin as described above with a set of stone models being poured from the patient's impressions. The next step sees a lab technician sawing each tooth away from the stone model and removing the stone material between the teeth. This process, called "resetting the model" sees most if not all of the teeth being similarly cut completely free of the stone model and then reattached to it using a special adhesive material called "sticky wax".

When resetting a model for the purpose of forming a series of progressive aligners in the laboratory setting, a laboratory technician would first reset the teeth in slightly more desirable positions than the positions that the stone teeth were in prior to cutting them free. Once the teeth are set with sticky wax in slightly more desirable positions, the technician will actually take an impression of the altered model itself in the same manner that impressions are taken from a living patient. From that impression of the altered stone model, a new stone model representing the slightly improved tooth positions will be poured. From that slightly improved stone model, an aligner will be sucked down.

After the first aligner is formed in this manner, the original modified stone model with its teeth reset to slightly more desirable positions is taken and placed in a container of hot water to heat it. Once sufficiently hot, the sticky wax softens, permitting the repositioning of the teeth into yet better and more desirable positions. This second repositioning is performed by the technician using thumb and index finger forces and once completed, yet another impression is taken of the reset model, and another aligner is created from a second stone model of that set-up. Through a third and forth (or more) series of such cycles, laboratory technicians could produce a series of progressive aligners similar to a series of Invisalign aligners, and they can do so without the use of digital computers, 3D imaging and rapid prototyping machines as required by the digital, 3D imaging approaches.

In comparing the digital Invisalign process to the manual methods of producing progressive aligners, it is important to note that the Invisalign process involves the production of a series of progressive aligners that are capable of orthodontically treating a patient from the beginning of treatment completely through to a finished result. In other words, in some cases, the Invisalign process can serve alone as the only treatment modality. Further, with the Invisalign process it is not necessary for any impressions other than the original impression of the patient's malocclusion to be taken. In contrast, a manually-formed series of progressive aligners are usually limited to treating only sub-objectives of a patient's treatment plan. Manually-produced aligners are used for intermediate treatment goals such as phase 1 tooth leveling and alignment, final aesthetic positioning of the teeth near the end of treatment, or for treating cases that have relapsed after the active phase of treatment has ended. It is possible for manually-produced aligners to be used to accomplish a patient's entire treatment from beginning to end like Invisalign aligners do, but such a series of aligners would require that multiple mid-course correction impressions be taken during the course of treatment. Conventional, manually-produced progressive aligners are typically produced in quantities of three to six sets, whereas Invisalign aligners are usually produced in quantities of from 15 to 35 sets.

Hilliard. Considering only aligner-based orthodontic therapy, independently of whether manual or digital production means are used to form them, orthodontists have amassed considerable experience in the use of aligners due to their long-term availability in orthodontics. Importantly, recent years have seen new ways of directing and amplifying the treatment forces aligners generate, as well as new ways of prolonging the duration of such forces have been devised. For example, U.S. Pat. No. 6,293,790, Heated Orthodontic Pliers, (Hilliard) discloses a system of steel dental pliers useful for modifying suck-down polymeric aligners. Commercially known as "Thermo-Pliers", they represent a series of instruments that are heated to a controlled temperature. Once hot, they are capable of local heat-softening and then thermally flowing the aligner material to form various types of thermo-formed features.

An example of the utility of Thermo-Pliers in augmenting aligner-based therapy involves a common problem faced by orthodontists which is the difficulty encountered in trying to rotate a tooth. Normally, the positional bias of the aligner, referred to above as an out-of-register relationship between the tooth-receiving socket formed in the aligner relative and the actual living tooth will produce force levels that are not fully capable of correcting the position of a tooth in terms of rotation. Rotations, as opposed to torqueing or tipping-type corrections are relatively difficult to achieve using aligners. To augment an aligner's capability to fully correct a tooth in terms of rotation, the attending doctor uses Thermo-Pliers to form an inward-facing bump in the structure of the aligner. Such a thermo-formed bump is positioned relative to a tooth's socket to produce a force vector of maximum mechanical advantage to rotate the tooth. For example, the bump may be placed at the distal, incisal, lingual position relative to a mandibular left lateral and another bump will be located at the mesial, labial incisal location for that tooth. This pair of co-working bumps creates a coupled rotational force that is very effective in rotating that tooth in a labial-mesial direction. A practitioner may allow partial rotational correction to be achieved just by the natural bias of the aligner. Perhaps six weeks later, the remaining correction can be achieved by activating the aligner through the installation of bumps via Thermo-Pliers.

Such bumps serve to focus energy stored in the local region adjacent to the bump as the elevated bump causes a local outward flexing of the aligner material away from the tooth. The bumps gather stored energy from a relatively wide area and impinge that energy onto the tooth at the most desirable locations to amplify the mechanical forces acting on that tooth.

Another one of the Thermo-Pliers series has features formed in its beaks that when heated are capable of forming a hook structure directly in the otherwise featureless material of an aligner's structure adjacent to the soft tissue or in the relatively flat material of the labial side of an incisor. Hooks are used for connecting orthodontic elastics that provide tractive forces between sectioned portions of an aligner (or the aligner and other fixed appliance structure) as needed during treatment. Similarly, other Thermo-Pliers are used to enhance the performance of aligners by installing other heat-formed features.

Orthodontic Aligner Auxiliaries. An entirely new methodology for using aligners is being mastered by orthodontists as the full treatment potential of aligner-based therapy is being revealed. Aligner-based treatment is popular with patients because aligners have several important advantages over conventional braces. Because patients like aligner-based therapy, and because it is effective, orthodontists seek out training and information related to aligner therapy. Along with the use of Thermo-Pliers, other means of amplifying, regulating and extending the corrective force generating capability of aligners are currently being promoted and extolled within the orthodontic profession.

As can be appreciated, the interior or tooth-contacting surfaces of the sockets of aligners completely surround and are in complete intimate physical contact with the tooth corresponding to the socket, as depicted in FIG. 1(a). In order for forces, such as those that are created through the installation of a bump to be effective, the interior surfaces on the opposite side of the socket must somehow be relieved to permit the movement of the tooth in that direction. In other words, an axiom of orthodontically moving teeth proposes that if you push a tooth in a certain direction, it will not move in that direction unless you have first created free space for that tooth to move into. Orthodontists will therefore alter aligners by discretely cutting away material to create such free space, or a window. Such windows can take many forms, but essentially are created by removing aligner material in the direction that the doctor wants the tooth to move. A window will be created, for example, on the labial side of a tooth if a bump is formed on the lingual side. This allows the focused force exerted on the lingual side of the tooth by the bump to not have an equal but opposite opposing force, and thus the tooth will in fact move labially into the window cut out of the aligner on its labial side.

Another example of relieving an aligner in order to tip a tooth inward or outward (known as correction in terms of torque) is this: Assuming a tooth is in its proper bodily position and only requires uprighting for desired orientation, a window can be cut into an aligner in an area limited to the incisal area of the tooth. With the installation of a bump at the incisal edge on the lingual side, the incisal edges of the crown will swing into the relief on the labial. Since in this example, the bulk of the aligner socket still holds the more gingival portions of the tooth in place, the tooth is uprighted without any bodily displacement from its desired position. In this general manner then, orthodontists can create pushing forces on one side of a socket, and discretely relieve the other side of the socket to very accurately tip, torque, rotate and bodily move the roots of teeth through the supporting alveolar bone.

As described above, Thermo-Pliers can form a force-creating bump extending inward into the tooth-accepting socket of an aligner. Just as easily however, an outward-extending bump can be formed which can be referred to as a "bubble". When forming a bubble, another outwardly extending bubble can be formed overlapping the first. While the Thermo-Pliers are hot, multiple bubbles can be formed near to, or overlapping each other, and in this way an area can be accurately shaped into one larger outward-extending bubble. Such bubbles may serve as an alternative to the window as described above. Bubbles can provide the relief or room for a tooth to move into in response to inwardly extending bumps on the opposite side of an aligner's socket.

Other useful adjuncts to aligner-based therapy have been achieved through the introduction of other aligner auxiliaries that function while installed or attached to the structure of an aligner, as disclosed in the applicant's U.S. Pat. No. 6,702,575, entitled "Orthodontic Aligner Auxiliary System," issued on Mar. 9, 2004, and incorporated herein by reference. For example, the following are several of the types of aligner auxiliaries that can be used in conjunction with conventional orthodontic aligners:

FIGS. 2 and 2(*a*) illustrate a simple tack 30 that can be installed in an opening 26 in an aligner 20. To accomplish the installation of a tack 30, a precisely-formed hole 26 of a pre-determined diameter is punched through the material of the aligner 20 using a hole-forming pliers configured to form a hole of a diameter slightly less than the shank 36 of the tack 30. Next, another pliers configured to push the head 32 of the tack 30 through the hole 26 is used. The tack 30 pops into position where it is tightly retained in the aligner 20 in the punched hole 26.

As can be appreciated, locating such a tack within an aligner to realize optimal physiological tooth-moving response is very similar to the effect achieved by installing a bump in an aligner. The use of a separate tack 30 as described however permits the forces delivered to a tooth to be progressively regulated through using a sequential series of progressively longer tacks 30*a*–30*c*, as shown in FIGS. 3(*a*) through 3(*c*). The shortest tack 30*a* would be installed in an aligner 20 first. The domed section would reside in the trough portion of the aligner 20 in direct contact with the tooth 10. After a certain degree of tooth movement is accomplished by the short tack 30*a*, (typically after two to six weeks) a medium-length tack 30*b* is installed and the short tack 30*a* is discarded. as the energy stored in the aligner's structure adjacent to the tack is spent through tooth position correction, a longer tack 30*c* can be installed after the medium tack 30*b* is similarly spent.

As can be appreciated, a treatment protocol using a series of progressively longer tacks permits patient participation. A doctor may instruct a patient or the patient's parents to install progressively longer tacks in sequence at home, thereby obviating the need and associated cost of an office visit.

The same sort of progressive activation as shown in FIGS. 3(*a*)–3(*c*) can be achieved via a series of tacks having a progression of elasticity. FIGS. 4(*a*)-4(*c*) show a series of tacks formed of progressively harder elastomeric materials.

Another methodology for regulating or controllably activating the forces that are directed to teeth via aligner auxiliary devices 30 that are installed directly in an aligner's structure is shown in FIGS. 5 and 6. Like tacks, they first require the punching of a hole 26 through the aligner 20. Such a hole 26 is pre-sized to inter-work with the male threads 38 of the aligner auxiliaries 30. In a sense, such devices can be considered to be self-threading or self-tapping as they screw into the aligner's hard but somewhat elastic material.

Similar to the threaded devices shown in FIGS. 5 and 6, the aligner auxiliary 30 shown in FIG. 7 requires a nut 40 to be installed directly into the opening 26 of the aligner 20. Note that instead of a round hole, the assembly shown in FIG. 7 requires a square or rectangular hole 26 of a predetermined size to be installed in an aligner 20. Such a hole can be formed in an aligner using a special square or rectangular die-punch pliers. The non-round configuration of the hole 26 prevents the nut 40 from rotating as the screw portion 42 is turned.

Tacks 30*a* and 30*b* can be used in combination to create a rotational couple as illustrated in FIGS. 8 and 8(*a*). As can be seen, positioning two aligner auxiliaries 30*a* and 30*b* relative to a mal-rotated tooth 10 serve to create a mechanical couple ideally tailored to rotate the tooth 10.

A tack 30 can serve as an anchor or hook for the attachment of latex or urethane elastomeric bands 52, as shown in FIG. 9. As such, its function is not involved in directly contacting a tooth to move it. The tractive forces produced by an elastic band 52 attached in this manner can serve to pull separate portions of an aligner together, or to pull the entire aligner, and the teeth contained in it collectively in one direction. Importantly, note that the tack 30 must engage holes pierced through an aligner, but if their inwardly extending portions contact the underlying tooth, undesirable uncontrolled tooth movement can occur. To prevent contact with the tooth, such devices are typically installed in an outset 28 formed in the aligner 20, as depicted in FIGS. 13(*a*) and 13(*b*). An outset 28 is a raised land or plateau that is formed outward, away from the teeth. The hole 26 formed through the aligner 20 that serves to retain the aligner auxiliary 30 is located at the center of the raised land 28 thereby allowing the aligner auxiliary 30 to be retained in the aligner 20, but importantly, held clear of the underlying tooth surface by the height of the land 28.

A plurality of tacks can be employed in combination with elastic bands to move multiple teeth or groups of teeth. As shown in FIG. 10, two tacks 30*a* and 30*b* have an elastic 52 stretched between the tacks. Such a configuration would require that the aligner first be partially or completely cut into two pieces 20*a* and 20*b*, and then the elastic 52 would serve to draw two groups of teeth together, performing a function known as space closing. Note, both aligner auxiliaries 30*a* and 30*b* would typically be attached to the aligner on outsets lest the tips of the tacks undesirably contact the teeth.

Outset tacks can be used to move multiple teeth or groups of teeth apart expansively with a compression coil spring 54. As shown in FIG. 11, the assembly spans to two sections of an aligner 20*a* and 20*b* that has been cut into two pieces. This assembly serves to drive the sections apart as well as the teeth contained in each section. Alternatively, an expansion jack screw 50 can be used to move multiple teeth or groups of teeth apart expansively, as shown in FIG. 12. Note that like the outset tacks 30*a* and 30*b* described above, the aligner auxiliaries that pop through the aligner are typically held clear of the underlying tooth surfaces by being installed in holes formed in outset or raised lands.

The aligner auxiliaries shown in FIGS. 9–12 are attached to aligners in cases where treatment require that the aligner be cut into two sections. These devices are employed to achieve relative movement between the two sections and in the process, move the teeth they control along with them. Such attachment means however are not limited to tractive or repellant forces between two sections of the same aligner. It should be understood that aligner auxiliaries could include a wide variety of devices intended to handle or generate forces directed to an aligner normally worn by a patient, or to handle extra-oral forces. For example, aligner auxiliaries can be used to handle forces directed to the patient's other arch. This type of device is held in position by an upper aligner located adjacent to the upper first molar. A similar attachment means is incorporated into the lower aligner. A bite jumper spring is compressed between these upper and lower attachments. Aligner auxiliaries can also be used to accept extra-oral devices such as face bows, lip bumpers and the like.

Tacks 30 can be placed to retain the entire orthodontic appliance relative to the patient's teeth and oral anatomy, as shown in FIG. 14. The retaining tacks 30 can be located and installed through holes 26 near the gingival margin between two teeth 10, just distal of the cupids. Another location for retentive tack is interproximal to the first molar and second bicuspid, but they can be installed at any other point determined appropriate by the CAD technician. Retentive tacks project inward from the buccal or labial, or outward from the lingual into the gingival interproximal area and act as clasps of sorts, ensuring the entire aligner 20 remains fully seated on all of the teeth 10 when in the mouth. Since the aligner 20 is generally resilient and somewhat flexible, as the aligner 20 is pushed downward on the teeth 10 into a seated position, the aligner 20 will flex outward along with the retaining tacks. Once fully seated, the resilience of the material will cause the aligner 20 to return to its original shape, thus urging the points of the retaining tacks 30 into gingival interproximal spaces. This relationship provides a gentle retentive lock serving to hold the aligner 20 in place.

Aligner auxiliaries can also serve a decorative function to enable patient self-expression, which a practitioner may encourage as part of a scheme to gain patient cooperation. Patient cooperation is vital for a successful finished orthodontic result. The devices 60 shown in FIGS. 15(a) and 15(b) serve no particular physiological function other than providing a patient with a means of self-expression. Such things can serve to add an element of fun and a vehicle for personal expression to orthodontic treatment for young patients, with the goal again being that of gaining of patient cooperation.

SUMMARY OF THE INVENTION

This invention provides a method for producing orthodontic aligners using a CAD system to modify a digital model of the patient's oral anatomy to incorporate features that accommodate attachment of aligner auxiliaries to the completed aligner(s).

These and other advantages, features, and objects of the present invention will be more readily understood in view of the following detailed description on and the drawings.

BRIEF DESCRIPTION OF THE DRAWINGS

The present invention can be more readily understood in conjunction with the accompanying drawings, in which:

FIG. 1 is a is an exploded perspective view of a patient's lower teeth 10 and a removable orthodontic aligner 20 with an opening 26.

FIG. 1(a) is a cross-sectional view of the orthodontic aligner 20 taken through one of its cavities 24.

FIG. 2 is an exploded detail perspective view of the opening 26 in the orthodontic aligner 20 and an orthodontic aligner auxiliary 30.

FIG. 2(a) is a front perspective view of the orthodontic aligner auxiliary 30 in FIG. 2.

FIGS. 3(a) through 3(c) are side elevational views of a progressive series of orthodontic aligner auxiliaries 30a–30c with tapered tips 34.

FIGS. 4(a) through 4(c) are side elevational views of a progressive series of orthodontic aligner auxiliaries 30a–30c with rounded tips 34.

FIG. 14 is an exploded detail perspective view showing orthodontic aligner auxiliaries 30 extending into the interproximal spaces between teeth 10 to exert a retentive force holding the aligner 20 in place.

FIGS. 15(a) and 15(b) are front perspective views of orthodontic aligner auxiliaries 60 that include ornamental or decorative designs.

DETAILED DESCRIPTION OF THE INVENTION

Figure 5:
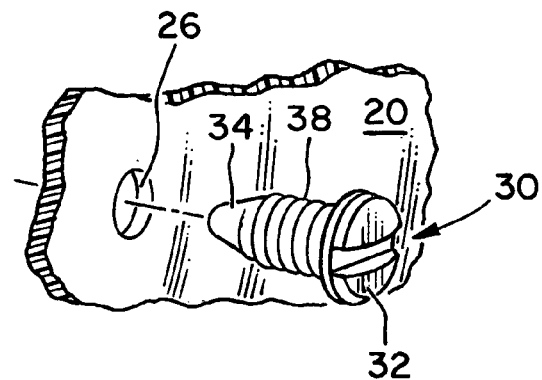
FIG. 5 is a detail perspective view of a threaded orthodontic aligner auxiliary 30 having a slotted head 32.
Figure 6:
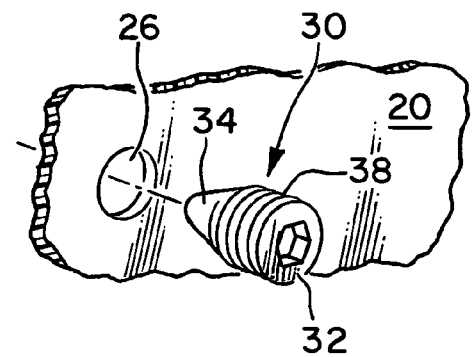
FIG. 6 is a detail perspective view of a threaded orthodontic aligner auxiliary 30 having a head 32 with a recess to accommodate an Allen wrench.
Figure 7:
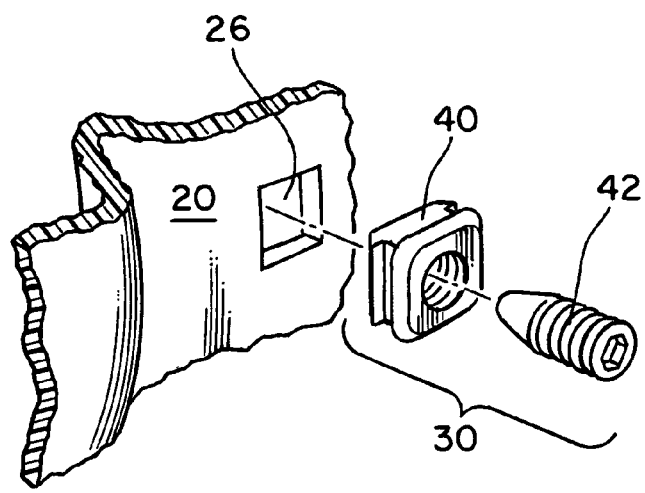
FIG. 7 is an exploded detail perspective of an orthodontic aligner auxiliary 30 having a nut 40 that snaps into an opening 26 of an aligner 20, and a screw 42 that threads into the nut 40.
Figure 8:
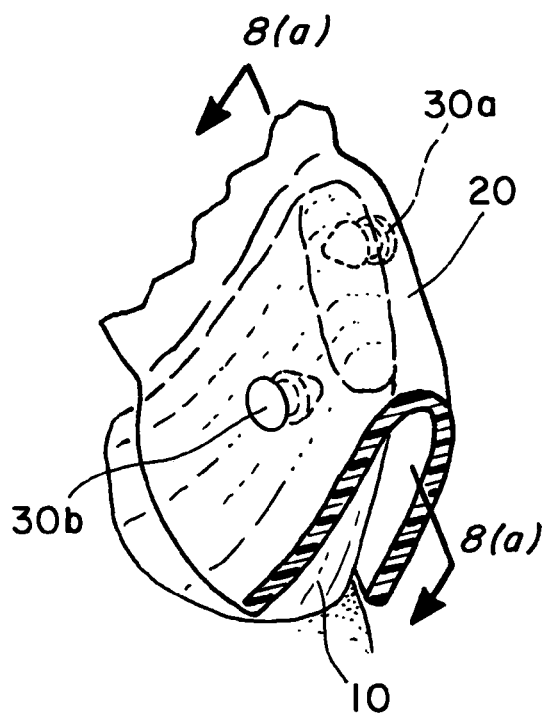
FIG. 8 is a detail perspective view of a portion of an aligner 20 with two orthodontic aligner auxiliaries 30a and 30b that exert a couple on a tooth 10.
Figure 8A:
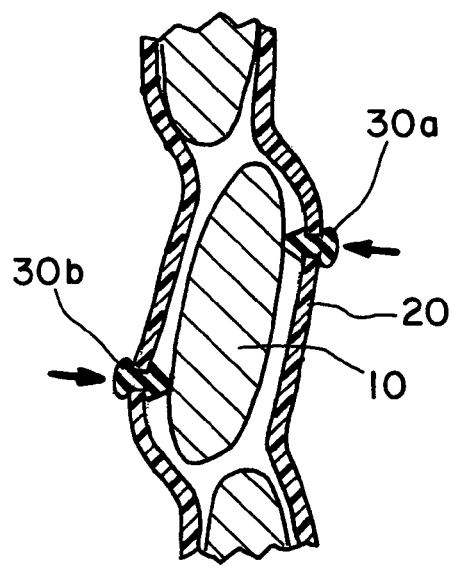
FIG. 8(a) is a horizontal cross-sectional view of an aligner 20 with two orthodontic aligner auxiliaries 30a and 30b that exert a couple on a tooth 10, corresponding to the FIG. 8.
Figure 9:
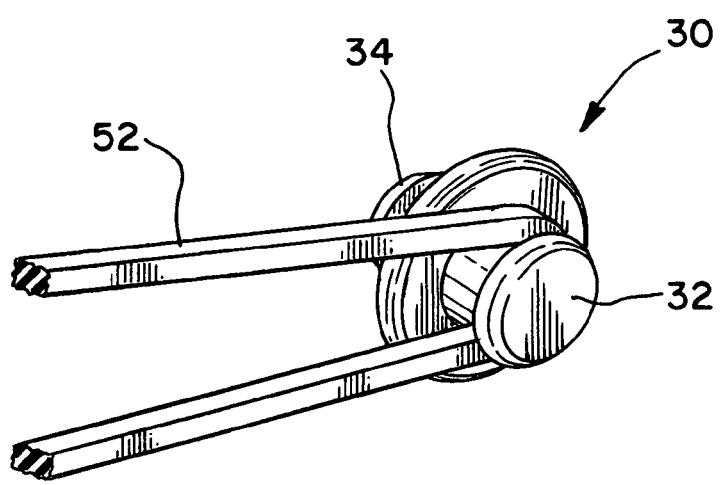
FIG. 9 is a detail perspective view of an aligner auxiliary 30 used to anchor an end of a rubber band 52.
Figure 10:
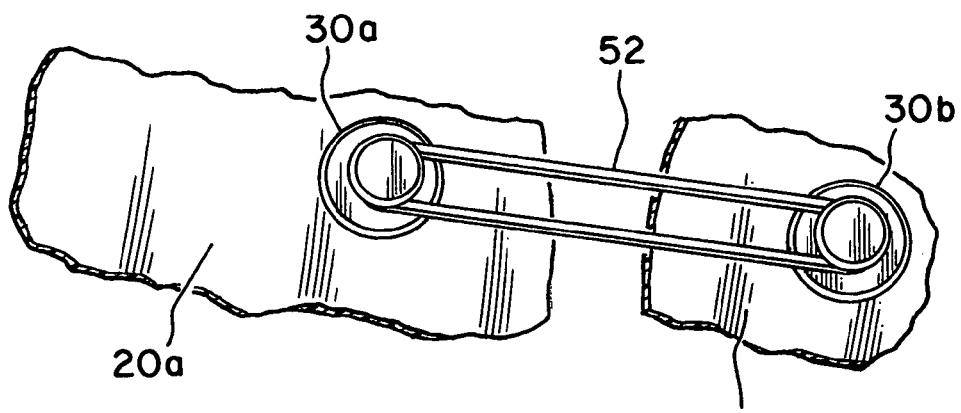
FIG. 10 is a detail perspective view of a rubber band 52 exerting a retractive force between two orthodontic aligner auxiliaries 30a and 30b.
Figure 11:
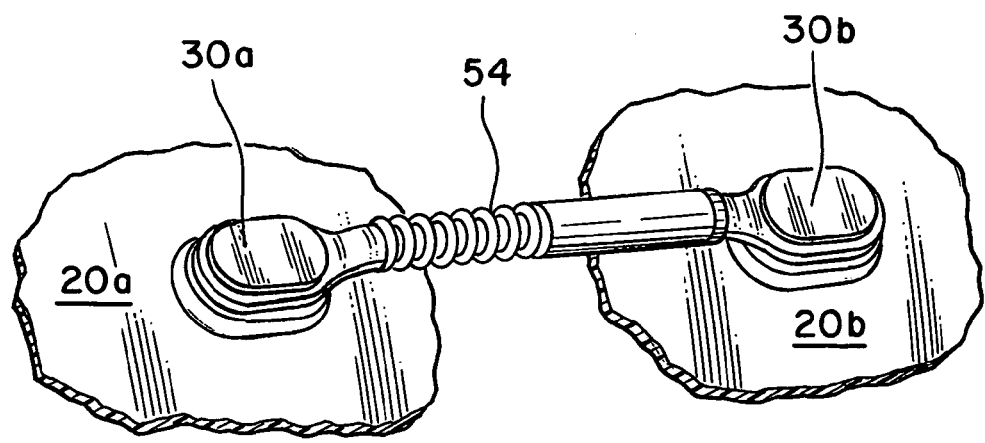
FIG. 11 is a detail perspective view of a spring 54 exerting an expanding force between two orthodontic aligner auxiliaries 30a and 30b.
Figure 12:
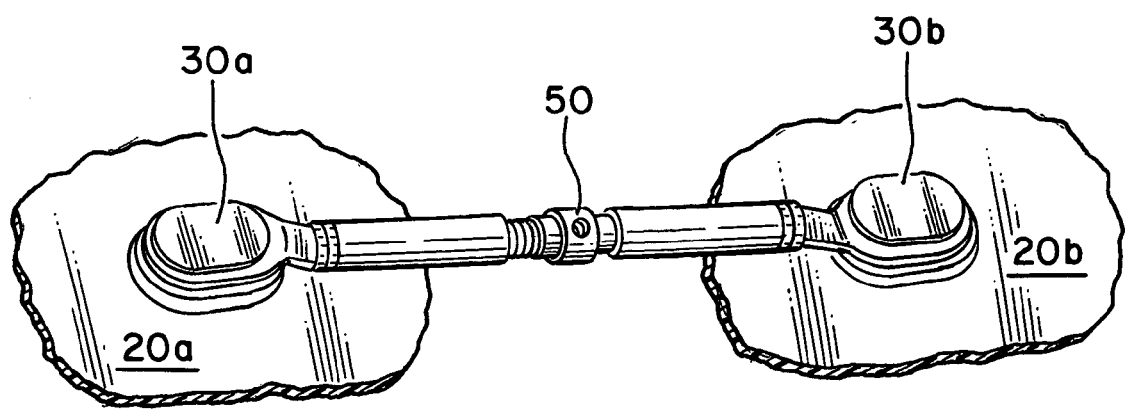
FIG. 12 is a detail perspective view of a connecting device 50 that can be used to exert either an expanding force or a retractive force between two orthodontic aligner auxiliaries 30a and 30b.
Figure 13A:
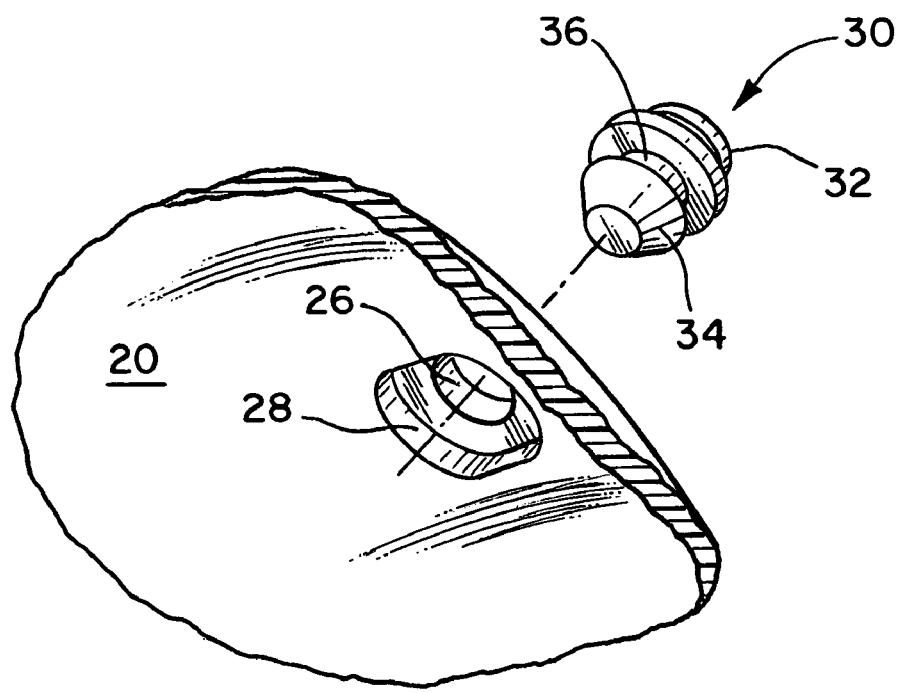
FIGS. 13(a) and 13(b) are detail perspective views of the interior surface of one of the cavities of the aligner 20 showing a recessed land 28 surrounding the opening 26 in the aligner 20, before and after insertion of an orthodontic aligner auxiliary 30.
Figure 13B:
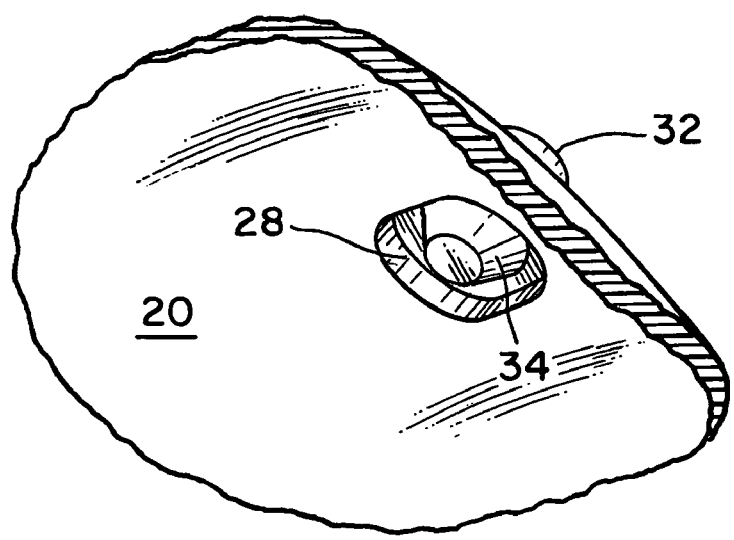
Figure 16:
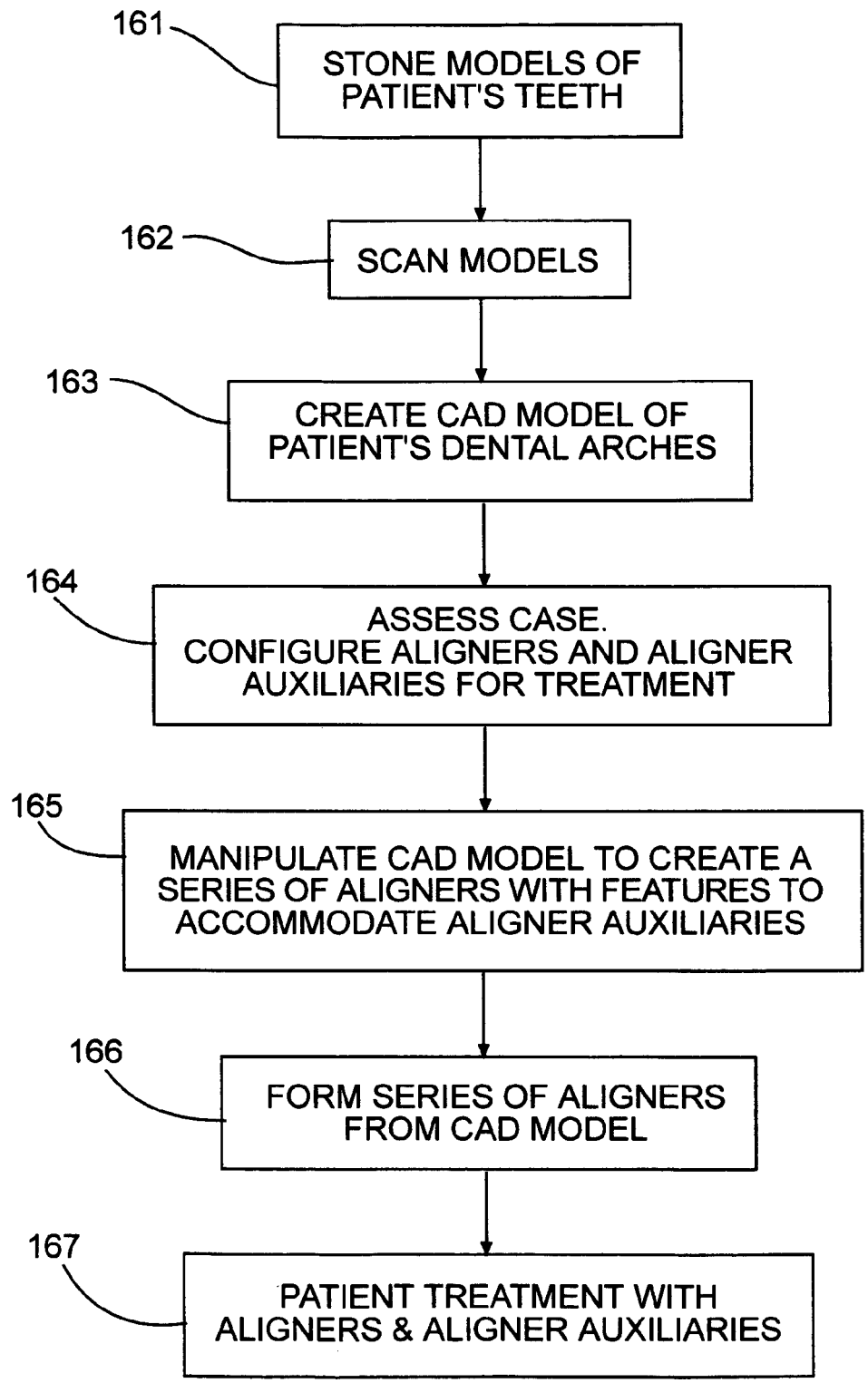
FIG. 16 is a flowchart providing a general overview of the steps in the present invention.

FIG. 16 is a flowchart providing a general overview of the present invention. To summarize, the present invention is a methodology to produce orthodontic aligners using a CAD system to modify a digital model of the patient's oral anatomy to incorporate features that accommodate attachment of aligner auxiliaries to the completed aligner(s). The present invention represents a convergence of the various advances made in aligner-based orthodontic treatment as may be accomplished by a CAD technician in the setting of a commercial orthodontic service center.

Initially, the relevant portions of the patient's oral anatomy are scanned to create a digital model in a format suitable for viewing and manipulation via a CAD system. As previously discussed, impressions of at least a portion of the patient's dental anatomy can be taken in the orthodontist's office using alginate, PVS or other conventional dental impression materials. These impressions are then used to make conventional stone models or other physical models (step 161 in FIG. 16), which are then shipped to the service center for processing. Alternatively, the impressions themselves could serve as the physical models that are shipped to the service center. In either case, the service center receives the patient's physical models and prescription form of instructions from the orthodontist and the case is logged into the service center's database.

The patient's models are then subjected to a scanning process and the resulting data for the upper and lower arches is stored in digital format (step 162 in FIG. 16) to create a CAD model of at least a portion of the patient's dental anatomy. The most frequently used means of converting an actual physical object into digital code for three-dimensional imaging, namely laser scanning, as well as other methods, first produce what is known as a "point cloud". The software will strive to rationalize the location of points known to be associated with features of the actual object with that same point located in other scans obtained while scanning the object from multiple angles. All of the points taken from multiple scans from different vantage angles will be overlapped and interpreted, allowing the software to create a complex surface represented by a cloud of perhaps a half-million individual points. Each of the points is assigned specific coordinates in three-dimensional space relative to a predetermined point of origin on the physical stone model of the patient's teeth. It should be understood that all of the points theoretically fall on the surface of the part being imaged and by viewing all of the points, a rough sort of visual image of the original part can be seen visually on a computer monitor.

Figure 17:
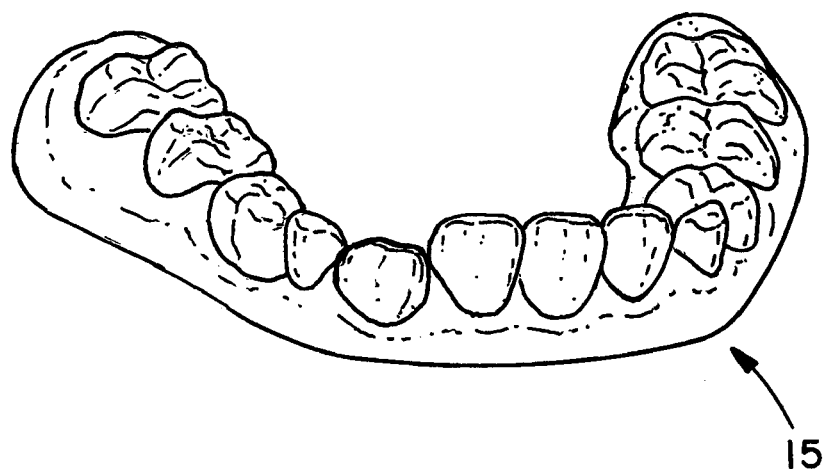
FIG. 17 is an image of the patient's lower teeth and gums produced by a CAD system.

Other software available to a CAD technician can be used to further process the point cloud into what is known as a true solid model that can be later manipulated and modified using solid-modeling CAD software (step 163 in FIG. 16). FIG. 17 is an example of the resulting CAD image 15 of the patient's teeth. However, some of the operations that a CAD technician needs to accomplish in processing an orthodontic patient's case can be performed at the initial point cloud phase.

Figure 18:
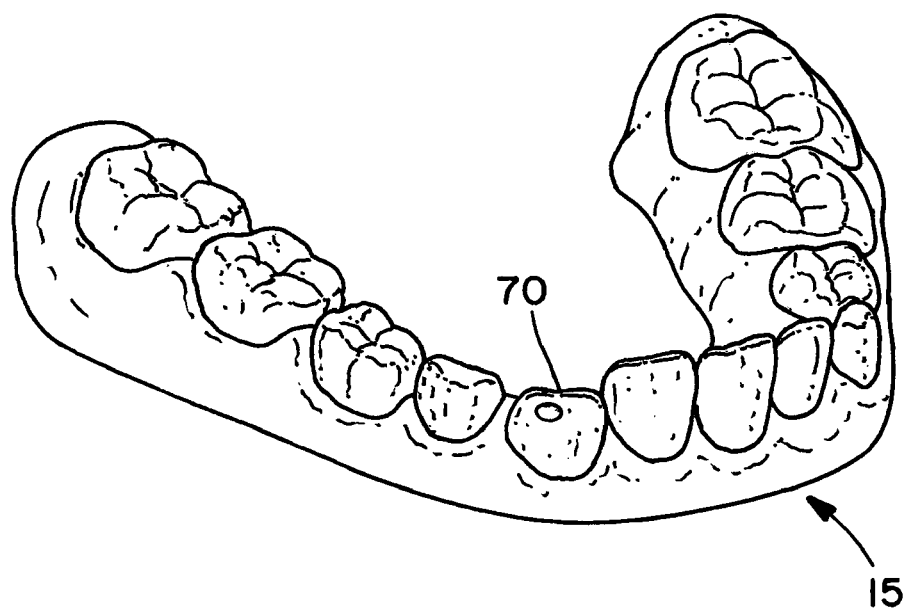
FIG. 18 is a CAD image showing a inwardly extending bump 70 formed on a tooth.

As an example of how a point cloud can be manipulated according to the present invention, commercially-available software permits a CAD technician to identify a region of points. The points inside such a region are assigned different properties than unaffected points outside the region. For example, a CAD technician may identify a region of points representing the occlusal region of a particular tooth from a scanned-in set of models. That region of points may be approximately the same size as an inwardly extending bump or outwardly extending bubble, for example. Conventional algorithms affecting how points within the identified region are dynamically linked allow the technician to grab any one point located near the center of the region and that point is then considered a master point. For example, the technician would accomplish this through manipulation of a digitizing puck on a digitizing tablet or with a mouse. The technician would tug on that master point. When tugged, all of the surrounding linked points within the identified region will to one degree or another move along with the master point being tugged in proportion to their relative distance from the master point. For example, points relatively near the master point will move the most whereas points more remote from the master point will move only a little. From this action, all of the points within the identified region will move to one degree or another and thereafter, the points inside the region will have moved inward into the general shape and appearance of a bump 70 as shown in FIG. 18.

Similarly, an outward-extending bubble can be formed by the technician by pulling a master point rather than pushing. Again, all of the points in a region will tag along to one degree or another as determined by the logic of how the points within the region are dynamically linked.

As an alternative to steps 161 and 162 in FIG. 16, a hand-held scanning wand (e.g., the Orometrix® system) can be used in the orthodontist's office to directly scan the patient's oral anatomy. The resulting digital data is then electronically transmitted to the orthodontic service center. Similarly, it is possible for the scanning methods described above to be directed to scanning the concave negative troughs directly from a set of dental impressions. This requires some changes to standard scanning techniques, but such a step is practical. There are clear advantages in scanning directly from the impressions, such as:

a. Standard alginate impressions can dry out and shrink over the span of a few days if not carefully stored in wet paper towels. If alginate impressions are sent into a commercial orthodontic service center and have been several days in shipment, it is possible that some dimensional change can occur. Polysiloxane, a non-algenic-acid-based impression material negates these problems, but it is expensive.

b. Currently, few orthodontic offices can financially justify laser scanning and imaging equipment, but it is known that scanning laser manufacturers are considering developing units specifically optimized for in-office use. Such units may be affordable and in that case, these units may become commonplace in the future. Inexpensive alginate impressions can be taken in the office and immediately scanned before shrinkage occurs.

c. If in-office scanning becomes commonplace in the future, one of the advantages to be enjoyed is that scanned data can be transferred easily to a commercial orthodontic service center via the internet.

There is also currently an emergence of computer-aided tomography (CAT) scanning equipment for dentistry. This equipment is smaller than the whole-body CAT scan machines typically seen in hospitals for example and is optimized to scan the human head only. Digital orthodontics must anticipate CAT scan type methods as playing a role in the future of three-dimensional dental imaging. Like laser-scanned data, CAT data can be readily converted into three-dimensional images and like scanned data, can be sent over the internet to an orthodontic service center for processing.

In one embodiment of the present invention, an orthodontic service center is established to implement the present invention and to manufacture custom aligners on the order of a doctor for individual patients. Like the Invisalign technician, whose focus is oriented toward making a simple series of progressive aligners, a technician using the present system would similarly use the same set of digital tools for the purpose of fabricating aligners optimized for use with aligner auxiliaries. Such aligners may be progressive in the Invisalign sense, but aligners of the present invention would not necessarily serve in treating an entire case.

Progressive-type aligners, as used with the Invisalign® program are indeed progressive in the sense that each subsequent aligner in a series moves the teeth slightly, making progress toward predetermined, ideal positions. However, for the purposes of the present invention, the term "progressive" need not necessarily mean progressively biasing cavities of each aligner. Due to the many degrees of activation afforded by the array of various types of direct aligner alterations that can be made such as with Thermo Pliers, and the array of separate auxiliary devices, progressive tooth movement may be achieved through the use of only one aligner. For example, direct tooth contacting short, medium and long tacks 3a, 3b and 3c may be used, or other devices with sequential elasticity (4c, 4b, and 4a) may be used. Various threaded devices 32 and 42 can be progressively activated, as can a jackscrew 50. Stainless steel or metallic auxiliaries such as a cantilever arm 24 can be progressively activated over time as is typical of orthodontic hardware. In this manner, aligners produced according to the present inventive methods can be considered as "progressive" in orthodontic treatment.

As a technician analyzes a patient's models visible on the computer monitor, the technician would see images representing a malocclusion at the beginning of treatment or partially-treated occlusion. Since the models can be used to generate a true three-dimensional image of the patient's oral anatomy, as shown in FIG. 17, the technician can dynamically rotate the dental topology for close scrutiny. The technician can sight across the virtual teeth from literally any angle or vantage point, including vantage points that would be anatomically impossible with a living patient, such as viewing from the rear of the mouth or vantage points occluded by bone and tissue.

Figure 19:
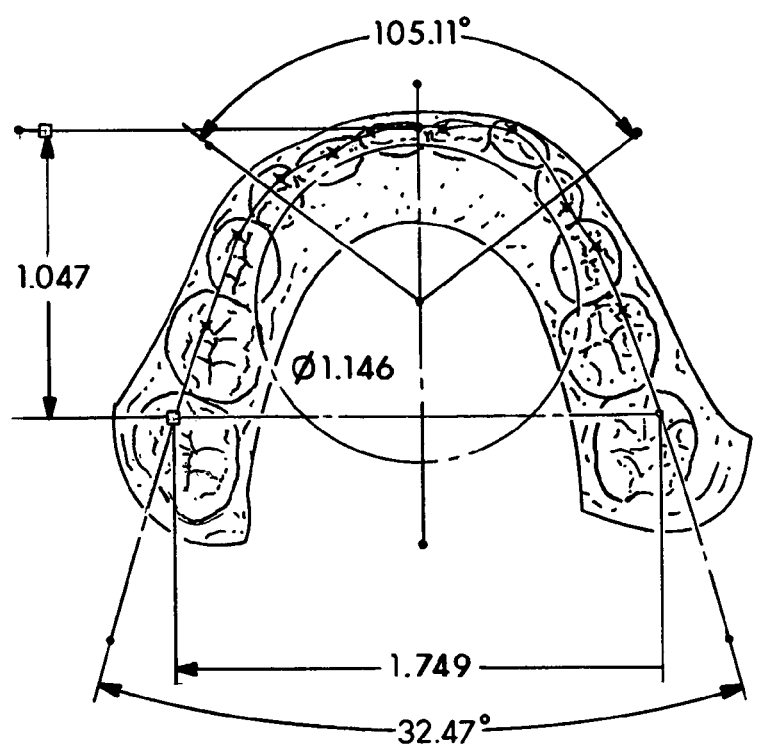
FIG. 19 is a CAD image with reference lines and dimensions.

Since the model exists in a virtual three-dimensional CAD space, the technician can assess the case and take measurements to quantify various criteria for treatment, such as upper versus lower arch length, arch width, inter-canine width, arch morphology as well as degree of open/deep bight, molar relationship, over jet, curve of Spee, and symmetry. The technician can also note primary, deciduous, missing and impacted teeth, and consult statistical anatomical values, all in light of the attending doctor's instructions/prescription. For example, the CAD software can be used by the technician to sketch any number of reference lines, centerlines, and such, as shown in FIG. 19. The dentition can be interrogated just like any solid model can be dimensioned with CAD software. As depicted in FIG. 19, two-dimensional and three-dimensional splines may be strung between features of the scanned-in surfaces. The technician may zoom in and magnify particular features for examination and decision making. Any number of features may be dimensioned from technician-specified reference lines or relative to other features of the anatomy. Generally, based on this process of measuring and examination, a technician may thereafter refer to and use known statistical data of established anatomical dental norms or other norms such as typical torque, tip prominence and arch form values found in patients of the same age, sex and ethnic characteristics. All of these activities are undertaken to arrive at optimal decision-making in preparation to designing a number of aligners and aligner auxiliaries to achieve treatment objectives (step 164 in FIG. 16).

Consider the challenges faced by a doctor standing at chair side holding a clear plastic aligner in his hands, trying to decide where best to form various bumps, bubbles, windows, various holes for activation devices, standoffs and outset lands and so on, that together will serve to activate tooth movement, as well as locate the myriad of aligner auxiliaries 30 described above. The reader should consider the challenges faced by such a doctor in contrast to the relative ease with which a CAD technician can make such decisions while viewing the entire virtual dentition. The technician can make such decisions with the aid of all of the technology and digital tools available at his or her disposal.

The technician has a wide array of analytical, measurement, and investigative tools at hand whereas a doctor attempting to make such decisions manually does not. It follows then that the CAD technician is in a much better position to make treatment decisions than the doctor at chair side. The technician can determine exactly where to locate aligner features such as inwardly extending bumps and outwardly extending bubbles. Various types of aligner auxiliaries 30 can also be optimally located by the CAD technician.

For example, the technician may identify a labially-flaired anterior tooth that requires uprighting. To accomplish such a correction with a suck-down aligner, the technician may opt to have a tack located at an exact position relative to that tooth. The technician will determine the ideal location that will maximize the tack's mechanical advantage for uprighting, and a location indicator (e.g., a divot marker 72) will be created exactly at that point. For that matter, the optimal location for piercing the aligner for the full array of aligner auxiliaries can best be determined by the CAD technician rather than the doctor attempting such an analysis manually while simultaneously addressing all of the other concerns and distractions involved when working with a real patient.

In general, the technician manipulates the CAD model to create a progressive series of aligners with features for accommodating aligner auxiliaries (step 165 in FIG. 16) for sequential use during the patient's orthodontic treatment. The technician working with the CAD system can create multiple virtual models representing the incremental, but progressive movement of teeth between the "as scanned" occlusion and the desired final occlusion. In addition, the technician can use the CAD system to move specific teeth according to treatment objectives to desired positions as would be considered ideal at the end of a specific phase of treatment for which aligner auxiliaries are to be employed. Movements accomplished by the CAD technician can include correction of individual teeth in terms of torque, tip, prominence, rotation, bodily movement, and to a degree intrusion and extrusion.

Figure 20:
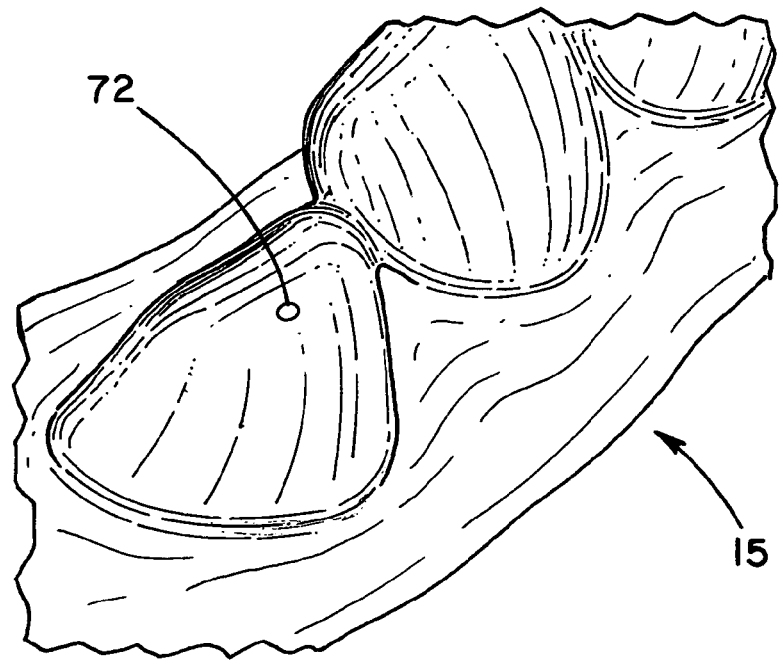
FIG. 20 is a CAD image showing a divot 72 formed on a tooth.

For example, the technician has the capability of zooming in on fine detail so that the computer monitor and the technician's field of vision accommodate only a single tooth being analyzed. In order to establish the optimal location for aligner auxiliaries, such as the pop-in tacks, a divot marker 72 can be installed on the model by the technician, as depicted in FIG. 20. A divot 72 is very similar to an inwardly extending bump 70 in FIG. 18, but it is spherical rather than elliptical and much smaller in diameter. To form a divot marker 72, the technician will identify a small round region of the point cloud at exactly the right position relative to the tooth under scrutiny. The technician will select and push a master point near the center of the region and all linked points will follow to a degree. The result is a series of discrete, sharply formed concavities located here and there as required around the arch to serve as visual markers indicating the position where holes will be installed relative to mal-positioned teeth.

Figure 21:
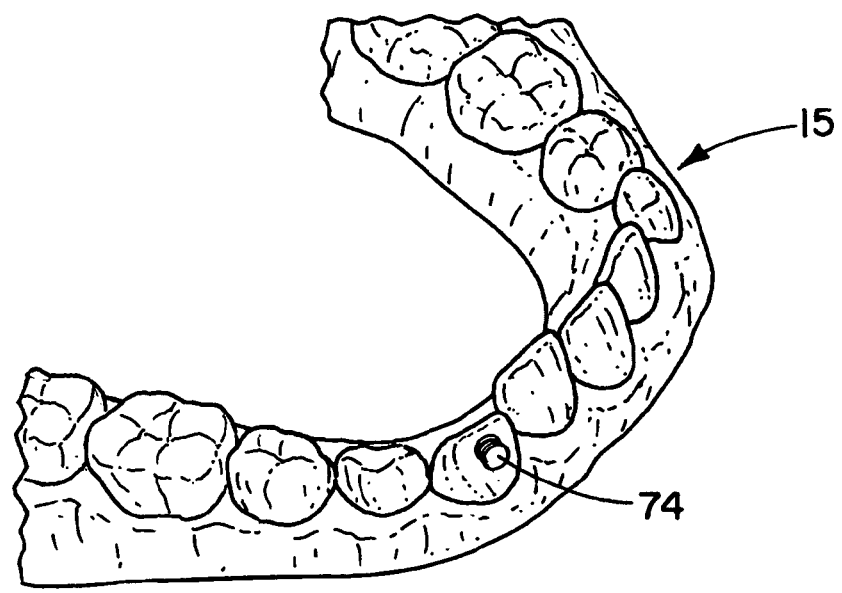
FIG. 21 is a CAD image showing a round outset 74 formed on a tooth.

Another point cloud-based operation is that of locating retaining tacks, as described in FIG. 21, that serve to hold the entire aligner in place in the mouth. In summary, technician-located marker divots would serve to mark locations for later installing plier-formed holes for the installation of the various types of aligner auxiliaries described above. If the technician decides that an aligner will be cut into multiple sections, a series of divots can be used to mark the location of the cuts or sinuses.

Preparing the model to form aligners with windows or outset lands requires methods that are different than those used to form bumps, bubbles and marker divots. Windows usually will have a plan-form or outline following the edges of a portion of the crown of a tooth or the entire crown of a tooth. Such shapes are more Cartesian than football-shaped bumps, bubbles and the round divot markers, and generally larger. Nonetheless, the CAD technician employing the methods of the present invention can form a polygonal boundary around the region of involved points of the point cloud, again creating a region that includes the linking of all of the points inside that boundary. Using a different point-linking algorithm however, the CAD technician can tug on a master point and all of the linked points of the point cloud within the designated region will follow equally. The point-linking logic will result in the entire region standing outward from the tooth surface. Such a feature will later be present in the actual formed aligner and will serve as a physical template or aid to the doctor or lab technician in cutting away aligner material to form a window. Since it is a raised plateau formed directly in the aligner, the doctor can easily see what material the technician had decided was necessary to remove.

As described above, elastic hooks and other aligner auxiliaries that pop-in can be installed in an outset land in order to ensure that their inwardly extending features do not contact teeth. In establishing outset lands on the virtual model, the technician will use the same point-linking algorithms as used for establishing the shape and location for a window where all of the points come along with a tugged master point equally.

As shown in FIG. 21, a round outset 74 has been formed by identifying a circular region of points and tugging all of those points outward perpendicularly away from the tooth surface. As can be appreciated, when an aligner is sucked down over such a pattern, a corresponding outset land will be formed in the aligner. Once formed in the aligner, a hole can then be pierced at the center of the flat top of the outset using a special plier, such as catalog item 82730, available from Raintree Essix, Metairie, La. Once a hole is pierced, any one of a group of pop-in aligner auxiliaries can be installed as needed.

As previously described, tacks may be offered in a progression of lengths characterized as short, medium and long. In such a series, the increase in length between a short tack and a medium tack and then to a long tack may be about 0.75 mm. In a case where, for example, a tooth needs only a slight correction, or the exact amount of correction needed falls in between the 0.75 mm increments between short, medium and long, a CAD technician may construct a discreet outset land of a precisely controlled height. For example, if a very short outset land were to be formed with a height of 0.37 mm, and a medium tack was installed in the outset land, the forces applied to the underlying tooth would be equal to a tack falling approximately half way between a short and medium tack. In this manner, devices of predetermined force-generating dimensions may be further calibrated as needed by mounting them in outset lands of selected heights.

Figure 22:
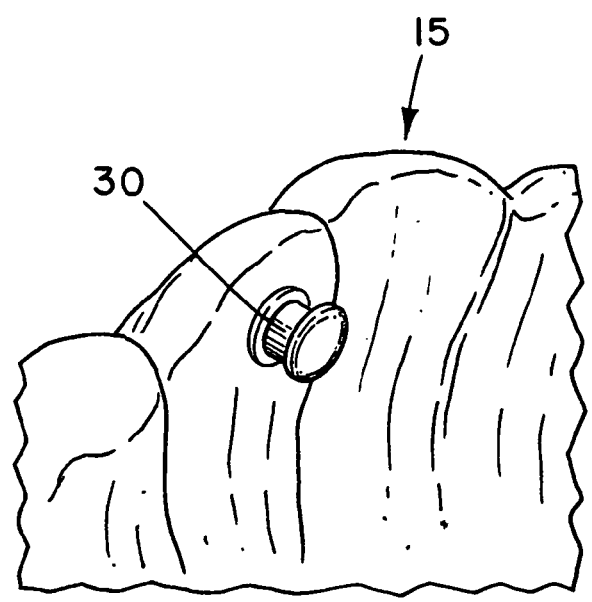
FIG. 22 is a CAD image showing the nose of a tack 30 mated onto a tooth.

Continuing with aspects of the present invention that lend themselves to very precisely controlled corrective movements of teeth such as those finishing corrections needed to attain final aesthetic positioning at the end of treatment, the following method is described through the example of a lower incisor that is undesirably inclined lingually by 1 mm. A CAD technician can form a virtual depression, similar to a divot or the depression associated with a bump, but sized and shaped to accommodate the nose of a tack. Such a geometrically discrete depression will be formed on the lingual side of the virtual tooth near its incisal edge. The CAD technician will form the depression in the lingually inclined lower incisor with a depth corresponding exactly to the amount of correction needed, in this case 1 mm deep. After the depression has been formed, the CAD technician will bring a virtual model of a medium tack into the virtual space and move it into close proximity with the depression. Using a CAD step known as "mating", the CAD technician will cause the nose of the tack to come into intimate contact with the depression so that the tack 30 and the virtual model become one solid structure, as shown in FIG. 22.

When a suck-down pattern is produced from this virtual model and an aligner is then sucked down over it, the resulting aligner will exhibit an outset feature adjacent to the undesirably lingually-oriented tooth coinciding with the exposed portions of a tack projecting lingually out of the referenced mandibular incisor. When viewing the aligner (particularly that cavity from the inside), it will be seen that the lingual-outset feature extending lingually from the subject lower incisor will have internal dimensions exactly corresponding to the exposed portions of the tack 30. The resilient nature of the aligner material permits the forcible placement of a tack into this outset feature. The tack will then be held and retained within the recess.

Most of the foregoing description of various actions and operations that can be executed by a CAD technician in preparing aligners have involved manipulations of the initial digital point cloud. Other types on operations that a CAD technician may need to undertake can best be accomplished after the point cloud has been further processed. Since such operations involve the use of CAD software to construct precise features on the virtual model, the first step in such a process is to convert the point cloud data into a surface, and then into what is known as a solid model. Software suitable for converting raw point cloud data into complex biological surfaces are available for this purpose from the sources listed below:

Raindrop Geomagic, Inc.
P.O. Box 12219
Research Triangle Park, N.C. 27709
Lightwave Enterprises, Inc.
2396 Innovation Way
Rochester, N.Y. 14624
Paraform, Inc.
3052 Bunker Hill
Santa Clara, Calif. 95054

Once the point cloud has been converted to a surface, the software is further used to close the surface. "Closing" here means this: It should be understood that the teeth and a small portion of the gums form a generally horseshoe shape. The surface defining the gums and teeth is in a mathematical sense infinitely thin. In CAD terminology, it is referred to as "light-weight". If the lightweight horseshoe-shaped dental model is viewed from its rear surface, for example, it is seen as merely a hollow shell. The software, in closing the surface in effect puts a bottom on it. At this stage it may still be considered an infinitely thin surface (i.e., lightweight), but with a bottom on it, it takes on a quality known as "watertight".

CAD software of the solid-modeling type such as is available from SolidWorks Corporation, 300 Baker Avenue, Concord, Mass. 01742 and PTC (Pro-Engineer), 140 Kendrick Street, Needham, Mass. 02494, has the capability of taking lightweight but watertight surfaces and converting them into standard, fully dense or fully solid models of the type normally handled by solid modeling CAD software.

Once converted to such a solid, the resulting dental model can be manipulated in a CAD environment in a conventional manner.

One of the operations that a CAD technician would then undertake according to the methods of the current invention is the installation of structures emerging directly out of the virtual solid CAD model. For example, a structure may be constructed that is needed for draft-retained inclusion devices. Two basic types of aligner auxiliaries were described above. One group of aligner auxiliaries were described as pop-in and a second group was described as devices that must be installed in outset lands to prevent them from undesirably contacting teeth. A third group of aligner auxiliaries referred to as "draft-retained devices" can also be accommodated with the present invention. Modification of the CAD model for attachment of draft-retained devices is preferably done after the point cloud has been converted to a solid CAD-manipulatable model. CAD manipulations of a solid model are precise and generally more sophisticated than operations involving the tugging or pushing on a point cloud.

In general terms, the technician manipulates the CAD model to create modified representations of the patient's dental anatomy to design a number of orthodontic aligners. In the simplest case, only one aligner may be sufficient. However, a progressive series of aligners can be designed for use during the course of orthodontic treatment. Typically, one modified representation of the patient's dental anatomy is created in the CAD system for each aligner to be produced. The present invention also enables the technician to manipulate the CAD model to incorporate a number of features to accommodate attachment of aligner auxiliaries to one or more of these aligners.

Figure 23:
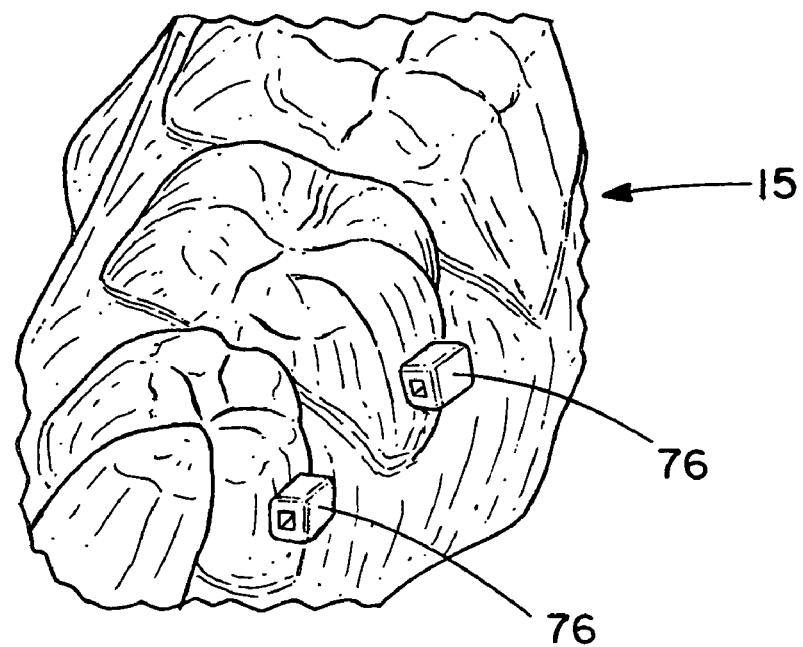
FIG. 23 is a CAD image showing a rectangular outset 76 formed on a tooth.

FIG. 23 illustrates the first step in producing an aligner capable of supporting a draft-retained device. The CAD technician constructs a raised feature 76 such as is shown in FIG. 23. Note that the raised structure 76 in FIG. 23 exhibits a significant negative draft in the direction of the tooth surface. As can be appreciated, a correspondingly-sized outset hollow feature formed over the raised structure 76 will result when an aligner is sucked down over it. Once an aligner has been sucked-down over such a pattern, the resulting aligner will likewise exhibit a structure feature resulting from the CAD-constructed feature described above. Since the aligner's material is somewhat flexible, the aligner can be temporarily distorted for removal from the negative-draft feature and thus removed from the suck-down pattern.

Figure 24:
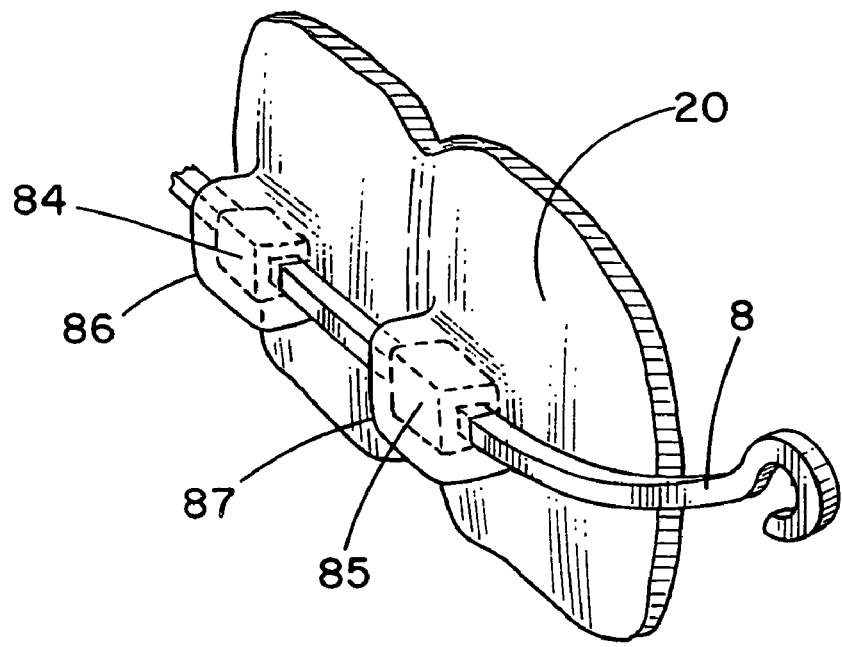
FIG. 24 is a detail perspective view of a fragmentary portion of an aligner 20 with draft-retained devices 84, 85 and a cantilever arm 82.

One example of this involves an aligner formed to accommodate draft-retained outward-extending features positioned on the second bicuspid and first molar, as illustrated in FIG. 24. A cantilever arm 82 formed from rectangular wire extends distally from floating draft-retained devices 84, 86 adjacent to the second bicuspid and first molar. The configuration functions to exert a lingually-directed force to correct a buccally-tipped second molar crown.

Figure 25:
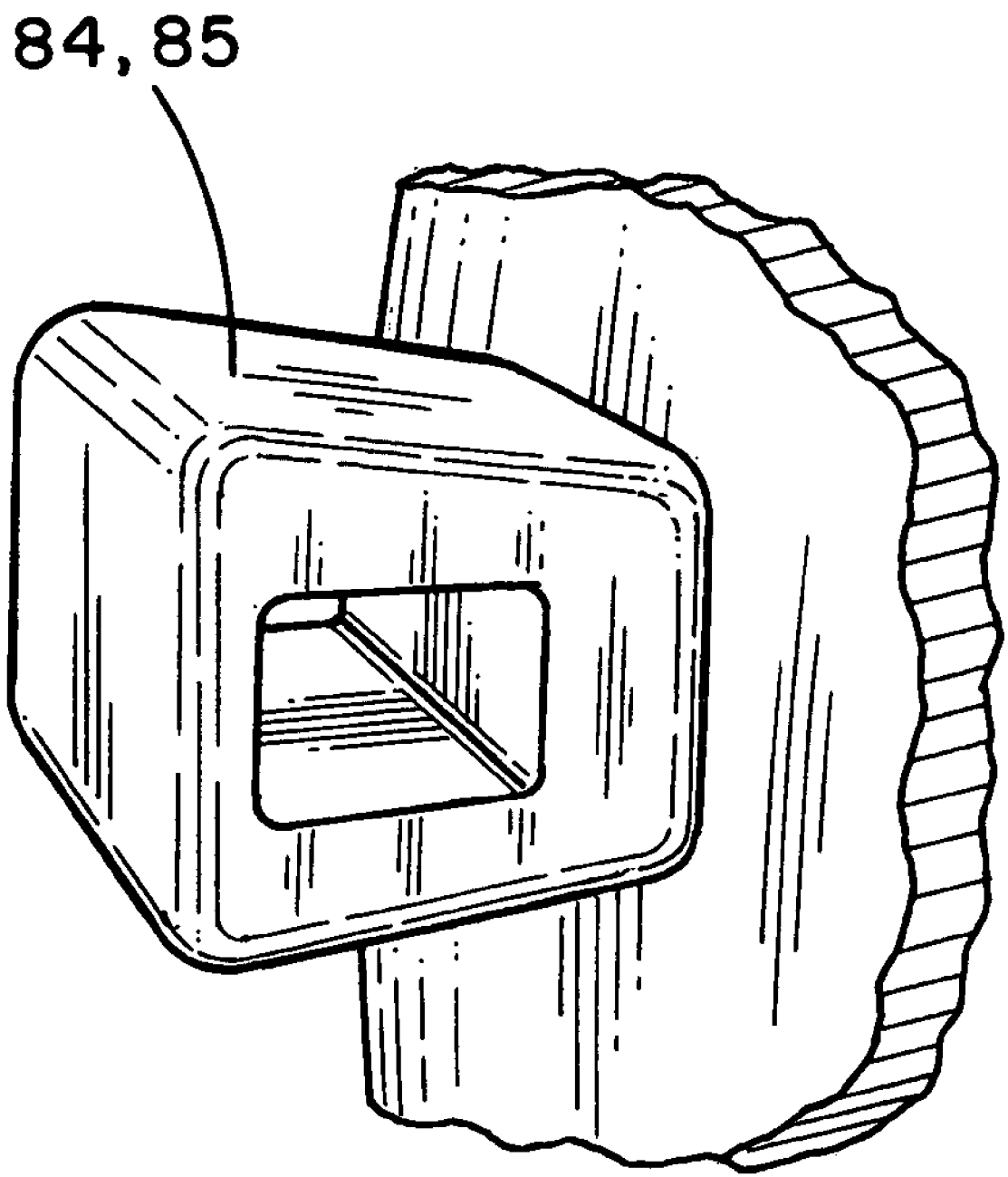
FIG. 25 is a perspective view of a draft-retained device 84, 85.

The free-floating draft-retained devices 84, 85 shown in FIG. 24 are sized to be retained within the outward-extending drafted outsets 86, 87 formed in the aligner 20. The original drafted outset structures constructed by the CAD technician on the patient's virtual model would be pre-sized, allowing the draft-retained devices 84, 85 to snap into the outsets 86, 87 of the aligner 20 from the inside surface of the aligner. Once snapped into place, the draft-retained devices 84, 85 would be loosely but positively retained within the outsets 86, 87 by the drafted contours of the aligner's features. Mesial and distally-extending holes are pierced through the aligner 20 in the areas adjacent to the mesial and distal ends of the draft-retained devices 84, 85. FIG. 25 is a perspective view of a draft-retained device 84, 95 with a 0.018×0.022 inch rectangular edgewise slot extending therethrough. The passage of correspondingly-sized, rectangularly shaped cantilever wire permits such a wire to be positioned and held at specifically useful angles and at selected positions in the mouth as needed to exert treatment forces. As can be appreciated, draft-retained devices can take multiple forms and can be utilized for a number of orthodontic treatment purposes and functions.

It should be understood that within the infrastructure of a commercial orthodontic service center providing services based on the present invention, a CAD technician will make a number of decisions regarding exactly how a case is to be treated based on all of the analytical tools at his or her disposal, including such pre-determined data as statistical tooth norms, along with the instructions from the attending orthodontist. For example, once the aligners have been designed and completed at a virtual level using the CAD model, the resulting modified set of models can be converted from CAD manipulatable code into code suitable for operating rapid prototyping machines that use stereo lithography methods to produce hard physical patterns. Patterns produced in this manner in turn serve as suck-down patterns for forming a series of actual aligners (step 166 in FIG. 16).

Once a series of aligners for an individual patient are formed via the suck-down process, they are trimmed and sequentially numbered. All of these post-forming steps are similar to the steps required by the Invisalign program. Once the series of sequential aligners is finished, a technician may use pliers to install all of the round, square and elliptical holes at the pre-identified locations marked by divot markers that are required by the pop-in aligner auxiliaries. The technician may also cut away windows and otherwise further modify the aligners according to the steps anticipated by the CAD technician. The technician may pop draft-retained devices into their concavities. The aligners may be cut for example to allow separate portions of an aligner to be pulled together by hooks and elastics or forced apart by a jack screw etc. The technician may package the various aligner auxiliaries in compartmentalized containers as aids for the doctor or staff in installing the various devices at their intended locations while at chair side with the patient. In any event, the series of aligners, and all related devices are packaged for shipment back to the attending orthodontist. Finally, the orthodontist treats the patient using the series of aligners and aligner auxiliaries, as previously discussed (step 167 in FIG. 16).

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A method for producing orthodontic aligners to accommodate aligner auxiliaries, said method comprising:

creating a CAD model of at least a portion of a patient's dental anatomy;

manipulating the CAD model to design an aligner having a polymeric shell with a plurality of cavities shaped to receive teeth and at least one feature to accommodate attachment of an aligner auxiliary to the aligner for exerting a therapeutic force on a desired portion of a patient's dental anatomy;

forming an orthodontic aligner from the CAD model incorporating the features to accommodate aligner auxiliaries; and attaching aligner auxiliaries to the features of the orthodontic aligner.

2. The method of claim 1 wherein the step of creating the CAD model further comprises the steps of:

creating a physical model of at least a portion of a patient's dental anatomy; and scanning the physical model to create the CAD model.

3. The method of claim 1 wherein the step of creating the CAD model further comprises scanning at least a portion of the patient's dental anatomy.

4. The method of claim 1 wherein the step of manipulating the CAD model further comprises manipulating the CAD model to design a plurality of aligners for sequential use during a patient's orthodontic treatment.

5. The method of claim 1 wherein the step of manipulating the CAD model further comprises forming a divot marker to indicate placement of an aligner auxiliary on the aligner.

6. The method of claim 5 wherein the step of forming an orthodontic aligner further comprises forming a opening in the aligner at the location of the divot marker to receive an aligner auxiliary.

7. The method of claim 1 wherein the step of manipulating the CAD model further comprises forming an outset land outward from a tooth to attach an aligner auxiliary to the aligner.

8. The method of claim 1 wherein the step of forming the orthodontic aligner further comprises:

forming a physical pattern from the CAD model representing at least a portion of the patient's dental anatomy as modified by the step of manipulating the CAD model; and forming an orthodontic aligner over the physical pattern.

9. The method of claim 1 wherein the step of manipulating the CAD model comprises modifying selected portions of the patient's dental anatomy in the CAD model to achieve desired positions during orthodontic treatment, and incorporating features to accommodate aligner auxiliaries.

10. A method for producing orthodontic aligners to accommodate aligner auxiliaries, said method comprising:

creating a CAD model of at least a portion of a patient's dental anatomy;

manipulating the CAD model to create a plurality of modified representations of a patient's dental anatomy for creating a plurality of aligners for sequential use during a patient's orthodontic treatment, wherein each aligner has a polymeric shell with a plurality of cavities shaped to receive teeth;

manipulating the CAD model to incorporate at least one feature to accommodate attachment of an aligner auxiliary to at least one of the aligners for exerting a therapeutic force on a desired portion of a patient's dental anatomy;

forming a series of orthodontic aligners from the CAD model incorporating the features to accommodate aligner auxiliaries; and attaching aligner auxiliaries to the features of the orthodontic aligners.

11. The method of claim 10 wherein the step of creating the CAD model further comprises the steps of:

creating a physical model of at least a portion of a patient's dental anatomy; and scanning the physical model to create the CAD model.

12. The method of claim 10 wherein the step of creating the CAD model further comprises scanning at least a portion of the patient's dental anatomy.

13. The method of claim 10 wherein the step of manipulating the CAD model further comprises forming a divot marker to indicate placement of an aligner auxiliary on the aligner.

14. The method of claim 13 wherein the step of forming an orthodontic aligner further comprises forming a opening in the aligner at the location of the divot marker to receive an aligner auxiliary.

15. The method of claim 10 wherein the step of manipulating the CAD model further comprises forming an outset land outward from a tooth to attach an aligner auxiliary to the aligner.

16. The method of claim 10 wherein the step of forming the orthodontic aligner further comprises:

forming physical patterns from the modified CAD model for each of the aligners; and forming the aligners over the physical patterns.

17. A method for producing orthodontic aligners to accommodate aligner auxiliaries, said method comprising:

creating a CAD model of at least a portion of a patient's dental anatomy;

manipulating the CAD model to create a modified representation of a patient's dental anatomy to design an orthodontic aligner having a polymeric shell with a plurality of cavities shaped to receive teeth and at least one feature to accommodate attachment of an aligner auxiliary to the aligner for exerting a therapeutic force on a desired portion of a patient's dental anatomy;

forming a physical pattern of the modified representation of a patient's dental anatomy from the modified CAD model;

forming an aligner over the physical pattern incorporating the features to accommodate aligner auxiliaries; and attaching aligner auxiliaries to the features of the orthodontic aligner.

18. The method of claim 17 wherein the step of creating the CAD model further comprises the steps of:

creating a physical model of at least a portion of a patient's dental anatomy; and scanning the physical model to create the CAD model.

19. The method of claim 17 wherein the step of creating the CAD model further comprises scanning at least a portion of the patient's dental anatomy.

20. The method of claim 17 wherein the step of manipulating the CAD model further comprises manipulating the CAD model to design a plurality of aligners for sequential use during a patient's orthodontic treatment.

21. The method of claim 17 wherein the step of manipulating the CAD model further comprises forming a divot marker to indicate placement of an aligner auxiliary on the aligner.

22. The method of claim 21 wherein the step of forming an orthodontic aligner further comprises forming a opening in the aligner at the location of the divot marker to receive an aligner auxiliary.

23. The method of claim 17 wherein the step of manipulating the CAD model further comprises forming an outset land outward from a tooth to attach an aligner auxiliary to the aligner.

* * * * *